US012383574B2

United States Patent
Chen et al.

(10) Patent No.: US 12,383,574 B2
(45) Date of Patent: Aug. 12, 2025

(54) APPLICATION OF CIRCULAR RNA IN PREPARING DRUG FOR TREATING SYSTEMIC LUPUS ERYTHEMATOSUS

(71) Applicant: CENTER FOR EXCELLENCE IN MOLECULAR CELL SCIENCE, CHINESE ACADEMY OF SCIENCES, Shanghai (CN)

(72) Inventors: Lingling Chen, Shanghai (CN); Li Yang, Shanghai (CN); Chuxiao Liu, Shanghai (CN); Xiang Li, Shanghai (CN); Fang Nan, Shanghai (CN)

(73) Assignee: Center for Excellence in Molecular Cell Science, Chinese Academy of Sciences, Shanghai (CN)

( * ) Notice: Subject to any disclaimer, the term of this patent is extended or adjusted under 35 U.S.C. 154(b) by 1023 days.

(21) Appl. No.: 17/433,568

(22) PCT Filed: Dec. 10, 2019

(86) PCT No.: PCT/CN2019/124160
§ 371 (c)(1),
(2) Date: Aug. 24, 2021

(87) PCT Pub. No.: WO2020/173171
PCT Pub. Date: Sep. 3, 2020

(65) Prior Publication Data
US 2022/0243270 A1 Aug. 4, 2022

(30) Foreign Application Priority Data
Feb. 25, 2019 (CN) .......................... 201910138059.X

(51) Int. Cl.
| A61K 31/713 | (2006.01) |
| A61K 45/06 | (2006.01) |
| A61P 37/02 | (2006.01) |
| C12Q 1/6883 | (2018.01) |

(52) U.S. Cl.
CPC ............ A61K 31/713 (2013.01); A61K 45/06 (2013.01); A61P 37/02 (2018.01); C12Q 1/6883 (2013.01); C12Q 2600/158 (2013.01); C12Q 2600/178 (2013.01)

(58) Field of Classification Search
CPC ....... A61K 31/713; A61K 45/06; A61P 37/02; A61P 37/06
See application file for complete search history.

(56) References Cited

FOREIGN PATENT DOCUMENTS

| CN | 107385013 A | 11/2017 |
| CN | 108441555 A | 8/2018 |
| CN | 109055529 A | 12/2018 |
| CN | 110643694 A | 1/2020 |

OTHER PUBLICATIONS

Lam et al., "Systemic Lupus Erythematosus: Primary Care Approach to Diagnosis and Management", American Family Physician, vol. 94, No. 4, pp. 284-294, Aug. 15, 2016. (Year: 2016).*
Li et al. (Feb. 20, 2018) "Comprehensive circular RNA profiles in plasma reveals that circular RNAs can be used as novel biomarkers for systemic lupus erythematosus" Clinica Chimica Acta 480, pp. 17-25.
Li et al. (May 23, 2018) "Circular RNA expression profile and potential function of hsa_circ_0045272 in systemic lupus erythematosus" Immunology 155(1) pp. 137-149.
Wang et al. (Jun. 8, 2018) "CircIBTK inhibits DNA demethylation and activation of AKT signaling pathway via miR-29b in peripheral blood mononuclear cells in systemic lupus erythematosus" Arthritis Research & Therapy 20(118), 10 pp.
International Search Report of International Patent Application PCT/CN2019/124160, mailed Mar. 24, 2020.
Extended European Search Report for EP Patent Application No. 19916672.9, dated Nov. 7, 2022, 11 pages.
Chen et al. (Mar. 1, 2017) "Circular RNA profile identifies circPVT1 as a proliferative factor and prognostic marker in gastric cancer" Cancer Lett. 388:208-219.
Holdt et al. (Oct. 9, 2018) "Circular RNAs as Therapeutic Agents and Targets" Front. Physiol. 9:1262; doi: 10.3389/fphys.2018.01262.
Li et al. (Jul. 21, 2016) "Circular RNAs and systemic lupus erythematosus" Exp. Cell Res. 346(2):248-254.
Li et al. (Aug. 2, 2018) "The Biogenesis, Functions, and Challenges of Circular RNAs" Mol. Cell 71(3):428-442.
Liu et al. (May 2, 2019) "Structure and Degradation of Circular RNAs Regulate PKR Activation in Innate Immunity" Cell 177(4):865-880.
Nallagatla et al. (Feb. 2011) "Regulation of innate immunity through RNA structure and the protein kinase PKR" Curr. Opin. Struct. Biol. 21(1) 119-127.
Xu et al. (Dec. 26, 2017) "Circular RNA hsa_circ_0003221 (circPTK2) promotes the proliferation and migration of bladder cancer cells" J Cell Biochem. 119(4):3317-3325.

* cited by examiner

*Primary Examiner* — Abigail Vanhorn
*Assistant Examiner* — Stephanie L Sullivan
(74) *Attorney, Agent, or Firm* — Leydig, Voit & Mayer, Ltd.

(57) ABSTRACT

The present invention provides use of a circular RNA with an incomplete double-stranded structure of 16 bp-33 bp in length and/or a promoting agent of the circular RNA with an incomplete double-stranded structure of 16 bp-33 bp in length in preparation of a medicament for treating systemic lupus erythematosus.

8 Claims, 8 Drawing Sheets
Specification includes a Sequence Listing.

APPLICATION OF CIRCULAR RNA IN PREPARING DRUG FOR TREATING SYSTEMIC LUPUS ERYTHEMATOSUS

CROSS-REFERENCE TO RELATED APPLICATIONS

This application is a U.S. National Stage Application filed under 35 U.S.C. § 371 of International Application No. PCT/CN2019/124160, filed Dec. 10, 2019 (Published as WO 2020/173171), which claims the benefit of and priority to Chinese Patent Application No. 201910138059.X filed Feb. 25, 2019, each of which are hereby incorporated by reference in their entireties.

INCORPORATION-BY-REFERENCE OF MATERIAL ELECTRONICALLY SUBMITTED

Incorporated by reference in its entirety herein is a computer-readable nucleotide sequence listing submitted herewith and identified as follows: 15,539 bytes ASCII (Text) file named "156-21US_SEQ_LIST_ST25.bct," created Apr. 22, 2022.

TECHNICAL FIELD

The present disclosure belongs to the field of biomedicine and particularly relates to use of circular RNAs (circRNAs) in preparation of a medicament for treating systemic lupus erythematosus.

BACKGROUND ART

Systemic Lupus Erythematosus (SLE) is a typical multi-organ multi-systemic autoimmune disease, with complex and diverse clinical and immunological manifestations such as immunological tolerance, dysregulation of lymphocyte function and disorder of lymphocyte apoptosis, complement deficiencies and immune complex clearance dysfunction, and dysregulation of cytokine secretion, almost encompassing the disorders of the entire immune system. Clinically, SLE mainly manifests as damage of multiple organs such as kidneys, nervous & mental system and hematological system. Early diagnosis in SLE patients before their vital organs are affected would be of great significance to prevent and treat SLE, improve the life quality for patients, and increase the productivity of patients. However, existing markers for biological diagnosis are mostly biochemical and immunological changes occurring after damage of organs, which cannot be used in early diagnose of organ involvement in SLE patients.

At present, the cause and pathogenesis of SLE are still not completely understood and are believed to be attributed to various factors such as familial inheritance, sexual hormone disturbance and environmental factors. Thus, there is still a lack of specific treatment means such that prevention and treatment of SLE cannot be enhanced fundamentally.

SUMMARY OF THE INVENTION

In order to solve the problem in the prior art, an objective of the present disclosure is to study expression of circRNAs in SLE and regulatory effect thereof on biological function of SLE and provide uses of expression products of circRNAs in diagnosis and treatment of SLE.

To achieve the above objective and other relevant objectives, the present disclosure adopts the following technical solutions:

A first aspect of the present disclosure provides use of a circRNA having an incomplete double-stranded structure of 16 bp-33 bp in length and/or a promoting agent of the circRNA having an incomplete double-stranded structure of 16 bp-33 bp in length in preparation of a medicament for treating SLE.

A second aspect of the present disclosure provides a method for treating SLE by administrating an effective amount of a circRNA having an incomplete double-stranded structure of 16 bp-33 bp in length and/or a promoting agent of the circRNA having an incomplete double-stranded structure of 16 bp-33 bp in length to a subject.

A third aspect of the present disclosure provides a medicament for treating SLE, including an effective dose of a circRNA having an incomplete double-stranded structure of 16 bp-33 bp in length and/or a promoting agent of the circRNA having an incomplete double-stranded structure of 16 bp-33 bp in length.

A fourth aspect of the present disclosure provides a combination of medicaments for treating SLE, including an effective dose of a circRNA having an incomplete double-stranded structure of 16 bp-33 bp in length and/or a promoting agent of a circRNA having an incomplete double-stranded structure of 16 bp-33 bp in length, and at least one additional medicament for treating SLE.

A fifth aspect of the present disclosure provides a method for treating SLE by administrating an effective amount of a circRNA having an incomplete double-stranded structure of 16 bp-33 bp in length and/or a promoting agent of a circRNA having an incomplete double-stranded structure of 16 bp-33 bp in length to a subject, and administrating an effective amount of an additional medicament for treating SLE to the subject and/or applying other means for treating SLE to the subject.

A sixth aspect of the present disclosure provides use of a circRNA having an incomplete double-stranded structure of 16 bp-33 bp in length and/or a promoting agent of a circRNA having an incomplete double-stranded structure of 16 bp-33 bp in length in preparation of a medicament having one or more effects selected from the group consisting of:
 (1) regulating the pathway of the circRNA to enhance the level of the circular RNA; and
 (2) directly increasing the level of the circRNA in cells.

A seventh aspect of the present disclosure provides use of a circRNA having an incomplete double-stranded structure of 16 bp-33 bp in length and/or a promoting agent of a circRNA having an incomplete double-stranded structure of 16 bp-33 bp in length in preparation or screening of a medicament for treating SLE.

An eighth aspect of the present disclosure provides use of a circRNA having an incomplete double-stranded structure of 16 bp-33 bp in length in preparation or screening of an agent for detecting systemic lupus erythematosus.

A ninth aspect of the present disclosure provides use of an agent for specifically recognizing a circRNA having an incomplete double-stranded structure of 16 bp-33 bp in length in preparation of a kit for detecting SLE.

A tenth aspect of the present disclosure provides a kit for detecting SLE, which includes at least an agent for specifically recognizing a circRNA having an incomplete double-stranded structure of 16 bp-33 bp in length.

Compared with the prior art, the present disclosure has the following beneficial effects:

According to the present disclosure, a pair of specific primers was designed to detect the expression of the circRNA having an incomplete double-stranded structure of 16 bp-33 bp in length. The expression of the circRNA having an incomplete double-stranded structure of 16 bp-33 bp in length in a patient with SLE was then detected and the result showed a significant decrease in expression level. Therefore, the circRNA can be used as a diagnostic marker for SLE. In addition, in the present disclosure, the cellular function of the gene of the circRNA having an incomplete double-stranded structure of 16 bp-33 bp in length was studied in vitro, in which the gene sequence of the circRNA was inserted into pZW1 vector to construct an expression vector for overexpression of the circRNA having an incomplete double-stranded structure of 16 bp-33 bp in length. Compared with controls transfected with an empty vector, peripheral blood mononuclear cells (PBMCs) from SLE patients in which the gene of the circRNA having an incomplete double-stranded structure of 16 bp-33 bp in length was overexpressed showed a significantly downregulated phosphorylation level of phosphorylase kinase (PKR), a downregulated expression of cytokine IFN-beta and a diagnostic gene for SLE in PBMCs and immune T cells of SLE patients. It has been shown that the gene of the circRNA having an incomplete double-stranded structure of 16 bp-33 bp in length and the expression product thereof can be used in preparation of a medicament for treating SLE. To sum up, the gene of the circRNA having an incomplete double-stranded structure of 16 bp-33 bp in length can serve as the diagnostic marker for SLE to diagnose SLE more accurately and rapidly. The gene expression product of the circRNA can serve as a molecule for preparing a medicament for the treatment of SLE and provide a new way for treating SLE.

DETAILED DESCRIPTION OF THE INVENTION

Figure 1:
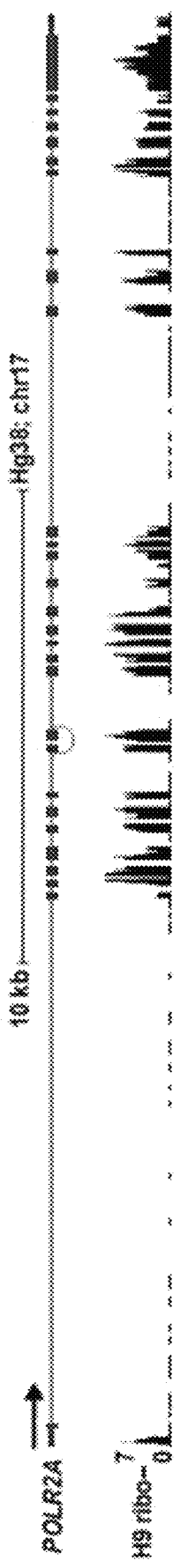
FIG. 1 illustrates a position map of circPOLR2A on a chromosome.

Before further describing the specific embodiments of the present disclosure, it should be understood that the protection scope of the present disclosure is not limited to the following specific embodiments. It should also be understood that the terms used in examples of the present disclosure are intended to describe specific embodiments and not meant to limit the protection scope of the present disclosure. Experimental methods in the following examples which are not specified with specific conditions are generally carried out according to conventional conditions or conditions recommended by manufacturers.

When numerical ranges are given in the examples, it should be understood that, unless otherwise specified in the present disclosure, two endpoints of each numerical range and any value between the two endpoints may be selected. Unless otherwise defined, all technical and scientific terms used in the present disclosure have the same meaning as commonly understood by those skilled in the art. In addition to the specific methods, equipment, and materials used in the examples, any methods, equipment, and materials equivalent or similar to those described in the examples of the present disclosure can be used to implement the present disclosure by those skilled in the art according to conventional knowledge and the description of the present disclosure.

Unless otherwise specified, the experimental methods, detection methods, and preparation methods disclosed in the present disclosure all adopt conventional techniques in molecular biology, biochemistry, chromatin structure and analysis, analytical chemistry, cell culture, recombinant DNA technology and related fields.

CircRNAs are recently discovered non-coding RNA molecules. Different from traditional linear RNAs, circRNAs are found with a covalently closed loop structure without 5' caps and 3' poly(A) tails. Recent studies show that circRNAs are predominantly formed by back-splicing, widely exist in various biological cells, and are characterized by extremely high structural stability, difficult degradation by exonuclease, tissue specificity and temporal and spatial specificity of expression thereof, etc. These characteristics allow circRNAs to have broad prospects in development and application of methods for the diagnosis and for the treatment of diseases.

An example of the present disclosure provides use of a circRNA having an incomplete double-stranded structure of 16 bp-33 bp in length and/or a promoting agent of a circRNA having an incomplete double-stranded structure of 16 bp-33 bp in length in preparation of a medicament for treating SLE. An incomplete double-stranded structure is defined as a stem-loop double-stranded structure formed by a RNA, in which both perfect complementary base pairing and a bulge or an internal loop formed by unpaired bases are present. The length of an incomplete double-stranded structure is calculated by the number of complementary base pairs. If there is a bulge or an internal loop and the number of unpaired bases forming the bulge or the internal loop is less than or equal to 4, it is still considered to be a single incomplete double-stranded structure, rather than multiple incomplete double-stranded structures.

As used herein, the circRNA having a special double-stranded structure and the circRNA having an incomplete double-stranded structure of 16 bp-33 bp in length refer to the same substance.

The circRNA having an incomplete double-stranded structure of 16 bp-33 bp in length used in the examples of the present disclosure is any one or more selected from the group consisting of circARID1B, circCAMSAP1, circCCNB1, circCNN2, circDHX34, circEPHB4, circEZH2, circFCHO2, circFGFR1, circFKBP8, circKIAA0368, circMBOAT2, circPIP5K1C, circPOLR2A, circPPP1CB, circPROSC, circPTK2, circPVT1, circRELL1, circSDHAF2, circSLC22A23, circSNHG4, circTBCD, circTMEM181, circUIMC1, and circVAPB.

The promoting agent of a circRNA having an incomplete double-stranded structure of 16 bp-33 bp in length used in the examples of the present disclosure is any one or more selected from the group consisting of circARID1B promoting agent, circCAMSAP1 promoting agent, circCCNB1 promoting agent, circCNN2 promoting agent, circDHX34 promoting agent, circEPHB4 promoting agent, circEZH2 promoting agent, circFCHO2 promoting agent, circFGER1 promoting agent, circFKBP8 promoting agent, circKIAA0368 promoting agent, circMBOAT2 promoting agent, circPIP5K1C promoting agent, circPOLR2A promoting agent, circPPP1CB promoting agent, circPROSC promoting agent, circPTK2 promoting agent, circPVT1 promoting agent, circRELL1 promoting agent, circSDHAF2 promoting agent, circSLC22A23 promoting agent, circSNHG4 promoting agent, circTBCD promoting agent, circTMEM181 promoting agent, circUIMC1 promoting agent, and circVAPB promoting agent.

The detailed information of the circRNAs is described below.

circARID1B (database ID: HSA_CIRCpedia_54093), with its genomic location being chr6: 157,357,968-157,406,039. Its corresponding linear gene is ARID1B (chr6: 157,256,600-157,473,538). The cyclization sequence has 286 bases. It includes the second and third exons of the ARID1B gene.

circCAMSAP1 (database ID: HSA_CIRCpedia_63397), with its genomic location being chr9: 13,8773,478-138,774,924. Its corresponding linear gene is CAMSAP1 (chr9: 138,700,333-138,799,005). The cyclization sequence has 425 bases. It includes the second and third exons of the CAMSAP 1 gene.

circCCNB1 (database ID: HSA_CIRCpedia_52305), with its genomic location being chr5: 68,470,703-68,471,364. Its corresponding linear gene is CCNB1 (chr5: 68,462,837-68,474,070). The cyclization sequence has 378 bases. It includes the sixth and seventh exons of the CCNB1 gene.

circCNN2 (database ID: HSA_CIRCpedia_24560), with its genomic location being chr19: 1,032,390-1,032,695. Its corresponding linear gene is CNN2 (chr19: 1,026,274-1,039,067). The cyclization sequence has 205 bases. It includes the third and fourth exons of the CNN2 gene.

circDHX34 (database ID: HSA_CIRCpedia_26297), with its genomic location being chr19: 47,865,732-47,865,950. Its corresponding linear gene is DHX34 (chr19: 47,852,538-47,885,961). The cyclization sequence has 218 bases. It includes the sixth exon of the DHX34 gene.

circEPHB4 (database ID: HSA_CIRCpedia_56001), with its genomic location being chr7: 100,410,368-100,410,830. Its corresponding linear gene is EPHB4 (chr7: 100,400,187-100,423,148). The cyclization sequence has 362 bases. It includes the tenth and eleventh exons of the EPHB4 gene.

circEZH2 (database ID: HSA_CIRCpedia_57174), with its genomic location being chr7: 148,543,561-148,544,397. Its corresponding linear gene is EZH2 (chr7: 148,504,464-148,581,441). The cyclization sequence has 253 bases. It includes the second and third exons of the EZH2 gene.

circFCHO2 (database ID: HSA_CIRCpedia_52515), with its genomic location being chr5: 72,370,568-72,373,320. Its corresponding linear gene is FCHO2 (chr5: 72,251,808-72,386,348). The cyclization sequence has 268 bases. It includes the nineteenth and twentieth exons of the FCHO2 gene.

circFGFR1 (database ID: HSA_CIRCpedia_60993), with its genomic location being chr8: 38,314,873-38,315,052. Its corresponding linear gene is FGFRI (chr8: 38,268,656-38,325,363). The cyclization sequence has 179 bases. It includes the second exon of the FGFRI gene.

circFKBP8 (database ID: HSA_CIRCpedia_25189), with its genomic location being chr19: 18,650,180-18,650,530. Its corresponding linear gene is FKBP8 (chr19: 18,642,561-18,654,387). The cyclization sequence has 259 bases. It includes the third and fourth exons of the FKBP8 gene.

circKIAA0368 (database ID: HSA_CIRCpedia_62244), with its genomic location being chr9: 114,148,656-114,154,104. Its corresponding linear gene is KIAA0368 (chr9: 114,122,972-114,246,637). The cyclization sequence has 435 bases. It includes the twenty-eighth, twenty-ninth, thirtieth and thirty-first exons of the KIAA0368 gene.

circMBOAT2 (database ID: HSA_CIRCpedia_42589), with its genomic location being chr2: 9,083,315-9,098,771. Its corresponding linear gene is MBOAT2 (chr2: 8,992,820-9,143,942). The cyclization sequence has 224 bases. It includes the second and third exons of the MBOAT2 gene.

circPIP5K1C (database ID: HSA_CIRCpedia_25726), with its genomic location being chr19: 3,660,963-3,661,999. Its corresponding linear gene is PIP5K1C (chr19: 3,630,179-3,700,477). The cyclization sequence has 249 bases. It includes the fourth and fifth exons of the PIP5K1C gene.

circPOLR2A (database ID: HSA_CIRCpedia_22419), with its genomic location being chr17: 7,402,357-7,402,810. Its corresponding linear gene is POLR2A (chr17: 7,387,685-7,417,933). The cyclization sequence has 336 bases. It includes the ninth and tenth exons of the POLR2A gene.

circPPP1CB (database ID: HSA_CIRCpedia_40659), with its genomic location being chr2: 29,006,772-29,011,675. Its corresponding linear gene is PPPICB (chr2: 28,974,612-29,025,806). The cyclization sequence has 224 bases. It includes the fifth and sixth exons of the PPPICB gene.

circPROSC (database ID: HSA_CIRCpedia_60919), with its genomic location being chr8: 37,623,043-37,623,873. Its corresponding linear gene is PROSC (chr8: 37,620,101-37,637,286). The cyclization sequence has 220 bases. It includes the second, third and fourth exons of the PROSC gene.

circPTK2 (database ID: HSA_CIRCpedia_60281), with its genomic location being chr8: 141,889,569-141,900,868. Its corresponding linear gene is PTK2 (chr8: 141,667,999-142,011,332). The cyclization sequence has 394 bases. It includes the third and fourth exons of the PTK2 gene.

circPRPSC (database ID: HSA_CIRCpedia_60029), with its genomic location being chr8: 128,902,834-128,903,244. Its corresponding linear gene is PVT1 (chr8: 128,806,779-129,113,499).

The cyclization sequence has 410 bases. It includes the second exon of the PVT1 gene.

circRELL1 (database ID: HSA_CIRCpedia_48457), with its genomic location being chr4: 37,633,006-37,640,126. Its corresponding linear gene is RELL1 (chr4: 37,592,422-37,687,998).

The cyclization sequence has 434 bases. It includes the fourth, fifth and sixth exons of the RELL1 gene.

circSDHAF2 (database ID: HSA_CIRCpedia_4841), with its genomic location being chr11: 61,205,096-61,205, 585. Its corresponding linear gene is SDHAF2 (chr11: 61,205,096-61,205,585). The cyclization sequence has 334 bases. It includes the second and third exons of the SDHAF2 gene.

circSLC22A23 (database ID: HSA_CIRCpedia_54791), with its genomic location being chr6: 3,410,421-3,416,089. Its corresponding linear gene is SLC22A23 (chr6: 3,269,196-3,457,256). The cyclization sequence has 259 bases. It includes the second and third exons of the SLC22A23 gene.

circSNHG4 (database ID: HSA_CIRCpedia_50464), with its genomic location being chr5: 138,614,015-138,614,818. Its corresponding linear gene is SNHG4 (chr5: 138,609,441-138,618,873). The cyclization sequence has 161 bases. It includes the third and fourth exons of the SNHG4 gene.

circTBCD (database ID: HSA_CIRCpedia_22969), with its genomic location being chr17: 80,858,526-80,869,665. Its corresponding linear gene is TBCD (chr17: 80,709,940-80,881,609). The cyclization sequence has 389 bases. It includes the seventeenth, eighteenth, nineteenth, twentieth, twenty-first and twenty-second exons of the TBCD gene.

circTMEM181 (database ID: HSA_CIRCpedia_54188), with its genomic location being chr6: 159,004,985-159,010,814. Its corresponding linear gene is TMEM181 (chr6: 158,957,468-159,049,522). The cyclization sequence has 324 bases. It includes the third, fourth and fifth exons of the TMEM181 gene.

circUIMC1 (database ID: HSA_CIRCpedia_51249), with its genomic location being chr5: 176,370,335-176,385,155. Its corresponding linear gene is UIMC1 (chr5: 176,332,006-176,433,409). The cyclization sequence has 397 bases. It includes the seventh, eighth, ninth and tenth exons of the UIMC1 gene.

circVAPB (database ID: HSA_CIRCpedia_34824), with its genomic location being chr20: 57,014,000-57,016,139. Its corresponding linear gene is VAPB (chr20: 56,964,175-57,026,156). The cyclization sequence has 258 bases. It includes the fourth and fifth exons of the VAPB gene. In an embodiment, the medicament for treating SLE has at least one effect selected from a group consisting of:

(1) reducing the PKR phosphorylation level in mononuclear cells from SLE patients; and (2) downregulating the expression of cytokine IFN-beta and diagnostic genes of systemic lupus erythematosus MX-1, LY-6E and IFIT3 in mononuclear cells and immune T cells of SLE patients. The promoting agent of a circRNA having an incomplete double-stranded structure of 16 bp-33 bp in length is a substance for enhancing the level of the circRNA having an incomplete double-stranded structure of 16 bp-33 bp in length. Specifically, (1) the circARID1B promoting agent refers to a substance for enhancing the level of circARID1B; (2) the circCAMSAP1 promoting agent refers to a substance for enhancing the level of circCAMSAP1; (3) the circCCNB1 promoting agent refers to a substance for enhancing the level of circCCNB1; (4) the circCNN2 promoting agent refers to a substance for enhancing the level of circCNN2; (5) the circDHX34 promoting agent refers to a substance for enhancing the level of circDHX34; (6) the circEPHB4 promoting agent refers to a substance for enhancing the level of circEPHB4; (7) the circEZH2 promoting agent refers to a substance for enhancing the level of circEZH2; (8) the circFCHO2 promoting agent refers to a substance for enhancing the level of circFCHO2; (9) the circFGFR1 promoting agent refers to a substance for enhancing the level of circFGFR1; (10) the circFKBP8 promoting agent refers to a substance for enhancing the level of circFKBP8; (11) the circKIAA0368 promoting agent refers to a substance for enhancing the level of circKIAA0368; (12) the circMBOAT2 promoting agent refers to a substance for enhancing the level of circMBOAT2; (13) the circPIP5K1C promoting agent refers to a substance for enhancing the level of circPIP5K1C; (14) the circPOLR2A promoting agent refers to a substance for enhancing the level of circPOLR2A; (15) the circPPP1CB promoting agent refers to a substance for enhancing the level of circPPP1CB; (16) the circPROSC promoting agent refers to a substance for enhancing the level of circPROSC; (17) the circPTK2 promoting agent refers to a substance for enhancing the level of circPTK2; (18) the circPVT1 promoting agent refers to a substance for enhancing the level of circPVT1; (19) the circRELL1 promoting agent refers to a substance for enhancing the level of circRELL1; (20) the circSDHAF2 promoting agent refers to a substance for enhancing the level of circSDHAF2; (21) the circSLC22A23 promoting agent refers to a substance for enhancing the level of circSLC22A23; (22) the circSNHG4 promoting agent refers to a substance for enhancing the level of circSNHG4; (23) the circTBCD promoting agent refers to a substance for enhancing the level of circTBCD; (24) the circTMEM181 promoting agent refers to a substance for enhancing the level of circTMEM181; (25) the circUIMC1 promoting agent refers to a substance for enhancing the level of circUIMC1; and (26) the circVAPB promoting agent refers to a substance for enhancing the level of circVAPB.

Specifically, the level of the circRNA having an incomplete double-stranded structure of 16 bp-33 bp in length can be enhanced by using various chemical, physical and biological methods. Such methods include but are not limited to:

(1) regulating the pathway of the circRNA having an incomplete double-stranded structure of 16 bp-33 bp in length to enhance the level of the circRNA having an incomplete double-stranded structure of 16 bp-33 bp in length; and (2) directly increasing the level of the circRNA having an incomplete double-stranded structure of 16 bp-33 bp in length in cells.

The level of the circRNA having an incomplete double-stranded structure of 16 bp-33 bp in length can be directly increased by overexpression of the circRNA having an incomplete double-stranded structure of 16 bp-33 bp in length.

Specifically, (1) the level of circARID1B can be enhanced by overexpression of circARID1B; (2) the level of circCAMSAP1 can be enhanced by overexpression of circCAMSAP1; (3) the level of circCCNB1 can be enhanced by overexpression of circCCNB1; (4) the level of circCNN2 can be enhanced by overexpression of circCNN2; (5) the level of circDHX34 can be enhanced by overexpression of circDHX34; (6) the level of circEPHB4 can be enhanced by overexpression of circEPHB4; (7) the level of circEZH2 can be enhanced by overexpression of circEZH2; (8) the level of circFCHO2 can be enhanced by overexpression of circFCHO2; (9) the level of circFGFR1 can be enhanced by overexpression of circFGFR1; (10) the level of circFKBP8 can be enhanced by overexpression of circFKBP8; (11) the level of circKIAA0368 can be enhanced by overexpression of circKIAA0368; (12) the level of circMBOAT2 can be enhanced by overexpression of circMBOAT2; (13) the level of circPIP5K1C can be enhanced by overexpression of circPIP5K1C; (14) the level of circPOLR2A can be enhanced by overexpression of circPOLR2A; (15) the level of circPPP 1CB can be enhanced by overexpression of circPPP 1CB; (16) the level of circPROSC can be enhanced by overexpression of circPROSC; (17) the level of circPTK2 can be enhanced by overexpression of circPTK2; (18) the level of circPVT1 can be enhanced by overexpression of circPVT1; (19) the level of circRELL1 can be enhanced by overexpression of circRELL1; (20) the level of circSDHAF2 can be enhanced by overexpression of circSDHAF2; (21) the level of circSLC22A23 can be enhanced by overexpression of circSLC22A23; (22) the level of circSNHG4 can be enhanced by overexpression of circSNHG4; (23) the level of circTBCD can be enhanced by overexpression of circTBCD; (24) the level of circTMEM181 can be enhanced by overexpression of circTMEM181; (25) the level of circUIMC1 can be enhanced by overexpression of circUIMC1; and (26) the level of circVAPB can be enhanced by overexpression of circVAPB.

Regulating the pathway of the circRNA having an incomplete double-stranded structure of 16 bp-33 bp in length can be enhancing the level of the circRNA having an incomplete double-stranded structure of 16 bp-33 bp in length by using an agonist of the circRNA having an incomplete double-stranded structure of 16 bp-33 bp in length.

Enhancing the level of the circRNA having an incomplete double-stranded structure of 16 bp-33 bp in length refers to increasing the circRNA having an incomplete double-stranded structure of 16 bp-33 bp in length. Preferably, compared with that before the enhancement, the level of the circRNA having an incomplete double-stranded structure of 16 bp-33 bp in length is enhanced by at least 10%, preferably at least 30%, further preferably at least 50%, more preferably 70%, and most preferably at least 90%.

The examples of the present disclosure have demonstrated that after directly increasing the level of the circRNA having an incomplete double-stranded structure of 16 bp-33 bp in length in cells by overexpression of the circRNA having an incomplete double-stranded structure of 16 bp-33 bp in length, the PKR phosphorylation level in mononuclear cells of SLE patients is decreased significantly, and the expression of cytokine IFN-beta and the diagnostic genes MX-1, LY-6E and IFIT3 for SLE in PBMCs and immune T cells of SLE patients are downregulated. It thus can be seen that the above-mentioned method of regulating the pathway of the circRNA having an incomplete double-stranded structure of 16 bp-33 bp in length can also result in significantly decreased PKR phosphorylation level in mononuclear cells of SLE patients and downregulated expression of cytokine IFN-beta and the diagnostic genes MX-1, LY-6E and IFIT3 for SLE in PBMCs and immune T cells of SLE patients. Hence, such methods are considered to be useful for treating SLE.

The medicament for treating SLE necessarily includes the circRNA having an incomplete double-stranded structure of 16 bp-33 bp in length and/or the promoting agent of the circRNA having an incomplete double-stranded structure of 16 bp-33 bp in length, and the circRNA having an incomplete double-stranded structure of 16 bp-33 bp in length and/or the promoting agent of the circRNA having an incomplete double-stranded structure of 16 bp-33 bp in length serve(s) as active ingredient for the effect described above.

In the medicament for treating SLE, the active ingredient having the effect described above can be merely the circRNA having an incomplete double-stranded structure of 16 bp-33 bp in length and/or the promoting agent of the circRNA having an incomplete double-stranded structure of 16 bp-33 bp in length, and can also include other molecule having similar effects. In other words, the circRNA having an incomplete double-stranded structure of 16 bp-33 bp in length and/or the promoting agent of the circRNA having an incomplete double-stranded structure of 16 bp-33 bp in length may be the only active ingredient or one of active ingredients.

The medicament for treating SLE can be a single ingredient substance or a multi-ingredient substance.

The medicament for treating SLE can be in various forms such as solid, liquid, gel, semi-liquid and aerosol, which will not be specifically limited.

The subject of the medicament for treating SLE is mainly mammals such as rodents and primates and the like.

A method for treating SLE provided in the present disclosure includes administrating an effective amount of a circRNA having an incomplete double-stranded structure of 16 bp-33 bp in length and/or a promoting agent of the circRNA having an incomplete double-stranded structure of 16 bp-33 bp in length to a subject.

The subject can be a mammal The mammal is preferably selected from the group consisting of rodent, artiodactyla animal, perissodactyla animal, lagomorph, primate, etc. The primate is preferably a monkey, an ape or a human.

The subject can be a patient having SLE or an individual looking forward to preventing or alleviating SLE. Alternatively, the subject can be isolated SLE cells from a patient having SLE or an individual looking forward to preventing or alleviating SLE.

The circRNA having an incomplete double-stranded structure of 16 bp-33 bp in length and/or the promoting agent of the circRNA having an incomplete double-stranded structure of 16 bp-33 bp in length can be administrated to a subject before, during or after receiving the treatment of SLE.

A medicament for treating SLE provided in the present disclosure includes an effective dose of a circRNA having an incomplete double-stranded structure of 16 bp-33 bp in length and/or a promoting agent of a circRNA having an incomplete double-stranded structure of 16 bp-33 bp in length.

In an embodiment, the medicament for treating SLE includes an effective dose of a circRNA having an incomplete double-stranded structure of 16 bp-33 bp in length and/or a promoting agent of a circRNA having an incomplete double-stranded structure of 16 bp-33 bp in length, and a pharmaceutically acceptable carrier.

The medicament for treating SLE necessarily includes the circRNA having an incomplete double-stranded structure of 16 bp-33 bp in length and/or the promoting agent of the circRNA having an incomplete double-stranded structure of 16 bp-33 bp in length, and the circRNA having an incomplete double-stranded structure of 16 bp-33 bp in length and/or the promoting agent of the circRNA having an incomplete double-stranded structure of 16 bp-33 bp in length are an active ingredient for the effects described above.

In the medicament for treating SLE, the active ingredient having the effects described above can be merely the circRNA having an incomplete double-stranded structure of 16 bp-33 bp in length and/or the promoting agent of the circRNA having an incomplete double-stranded structure of 16 bp-33 bp in length, and can also include other molecules having similar effects.

In other words, the circRNA having an incomplete double-stranded structure of 16 bp-33 bp in length and/or the promoting agent of the circRNA having an incomplete double-stranded structure of 16 bp-33 bp in length may be the only active ingredient or one of active ingredients.

The medicament for treating SLE can be a single ingredient substance or a multi-ingredient substance.

The medicament for treating SLE can be in various forms such as solid, liquid, gel, semi-liquid and aerosol, which will not be specifically limited.

The subject of the medicament for treating SLE is mainly mammals such as rodents and primates and the like.

A combination of medicaments for treating SLE provided in the present disclosure includes an effective dose of a circRNA having an incomplete double-stranded structure of 16 bp-33 bp in length and/or a promoting agent of a circRNA having an incomplete double-stranded structure of 16 bp-33 bp in length, and at least one additional medicament for treating SLE.

The combination of medicaments for combination treatment can be in any one of the following forms:

I) The circRNA having an incomplete double-stranded structure of 16 bp-33 bp in length, the promoting agent of the circRNA having an incomplete double-stranded structure of 16 bp-33 bp in length and the additional medicament for treating SLE are prepared into individual preparations, respectively. The dosage form of the formulations may be the same or different, and the administration route thereof may be the same or different.

When the additional medicament for treating SLE is an antibody, parenteral administration is commonly used. When the additional medicament for treating SLE is a chemical medicament, administration route can be diversified, such as gastrointestinal administration and parenteral administration. Generally, a known administration route for each chemical medicament is recommended.

II) The circRNA having an incomplete double-stranded structure of 16 bp-33 bp in length and/or the promoting agent of the circRNA having an incomplete double-stranded structure of 16 bp-33 bp in length and the additional medicament for treating SLE are formulated into a compound preparation. A compound preparation formulated by the circRNA having an incomplete double-stranded structure of 16 bp-33 bp in length and/or the promoting agent of the circRNA having an incomplete double-stranded structure of 16 bp-33 bp in length and the additional medicament for treating SLE can be applied when the circRNA having an incomplete double-stranded structure of 16 bp-33 bp in length and/or the promoting agent of the circRNA having an incomplete double-stranded structure of 16 bp-33 bp in length and the additional medicament for treating SLE are administrated via the same administration route and administrated simultaneously.

A method for treating SLE provided in the present disclosure includes administrating a circRNA having an incomplete double-stranded structure of 16 bp-33 bp in length and/or a promoting agent of a circRNA having an incomplete double-stranded structure of 16 bp-33 bp in length to a subject and administrating an effective amount of an additional medicament for treating SLE to the subject and/or applying other means for treating SLE to the subject.

An effective amount of the circRNA having an incomplete double-stranded structure of 16 bp-33 bp in length and/or the promoting agent of the circRNA having an incomplete double-stranded structure of 16 bp-33 bp in length and an effective amount of at least one additional medicament for treating SLE can be administrated simultaneously or sequentially.

In view that the circRNA having an incomplete double-stranded structure of 16 bp-33 bp in length is a therapeutic target for SLE first discovered in the present disclosure, the circRNA having an incomplete double-stranded structure of 16 bp-33 bp in length and/or the promoting agent of the circRNA having an incomplete double-stranded structure of 16 bp-33 bp in length can at least achieve an additive therapeutic effect in combination medication with the additional medicament for treating SLE other than the circRNA having an incomplete double-stranded structure of 16 bp-33 bp in length and/or the promoting agent of the circRNA having an incomplete double-stranded structure of 16 bp-33 bp in length, so that the treatment effect of SLE is further enhanced.

The additional medicament for treating SLE includes but is not limited to: antibodies, chemical medicaments or targeted medicaments.

The circRNA having an incomplete double-stranded structure of 16 bp-33 bp in length and/or the promoting agent of the circRNA having an incomplete double-stranded structure of 16 bp-33 bp in length can be administrated gastrointestinally or parenterally. The additional medicament for treating SLE can be administrated gastrointestinally or parenterally.

Examples of the present disclosure provide use of one or more of circRNAs having an incomplete double-stranded structure of 16 bp-33 bp in length and/or promoting agents for circRNAs having an incomplete double-stranded structure of 16 bp-33 bp in length in preparation of a medicament having any one or more effects selected from the group consisting of:

(1) reducing the PKR phosphorylation level in mononuclear cells of SLE patients; and (2) downregulating the expression of cytokine IFN-beta and diagnostic genes MX-1, LY-6E and IFIT3 for SLE in PBMCs and immune cell T cells of SLE patients.

Examples of the present disclosure provide use of use of a circRNA having an incomplete double-stranded structure of 16 bp-33 bp in length in preparation or screening of a medicament for treating SLE.

In an embodiment, the circRNA having an incomplete double-stranded structure of 16 bp-33 bp in length serves as a target. Specifically, one or more of circARID1B, circCAMSAP1, circCCNB1, circCNN2, circDHX34, circEPHB4, circEZH2, circFCHO2, circFGFR1, circFKBP8, circKIAA0368, circMBOAT2, circPIP5K1C, circPOLR2A, circPPP1CB, circPROSC, circPTK2, circPVT1, circRELL1, circSDHAF2, circSLC22A23, circSNHG4, circTBCD, circTMEM181, circUIMC1 and circVAPB serve as target.

The use specifically refers to, with the circRNA having an incomplete double-stranded structure of 16 bp-33 bp in length as a object, screening candidate substances to find out a promoting agent of the circRNA having an incomplete double-stranded structure of 16 bp-33 bp in length as an alternative medicament for treating SLE.

The promoting agent of the circRNA having an incomplete double-stranded structure of 16 bp-33 bp in length can be an overexpression agent for the circRNA having an incomplete double-stranded structure of 16 bp-33 bp in length. Specifically, (1) the circARID1B promoting agent is a circARID1B overexpression agent; (2) the circCAMSAP1 promoting agent is a circCAMSAP1 overexpression agent; (3) the circCCNB1 promoting agent is a circCCNB1 overexpression agent; (4) the circCNN2 promoting agent is a circCNN2 overexpression agent; (5) the circDHX34 promoting agent is a circDHX34 overexpression agent; (6) the circEPHB4 promoting agent is a circEPHB4 overexpression agent; (7) the circEZH2 promoting agent is a circEZH2 overexpression agent; (8) the circFCHO2 promoting agent is a circFCHO2 overexpression agent; (9) the circFGFR1 promoting agent is a circFGFR1 overexpression agent; (10) the circFKBP8 promoting agent is a circFKBP8 overexpression agent; (11) the circKIAA0368 promoting agent is a circKIAA0368 overexpression agent; (12) the circMBOAT2 promoting agent is a circMBOAT2 overexpression agent; (13) the circPIP5K1C promoting agent is a circPIP5K1C overexpression agent; (14) the circPOLR2A promoting agent is a circPOLR2A overexpression agent; (15) the circPPP1CB promoting agent is a circPPP1CB overexpression agent; (16) the circPROSC promoting agent is a circPROSC overexpression agent; (17) the circPTK2 promoting agent is a circPTK2 overexpression agent; (18) the circPVT1 promoting agent is a circPVT1 overexpression agent; (19) the circRELL1 promoting agent is a circRELL1 overexpression agent; (20) the circSDHAF2 promoting agent is a circSDHAF2 overexpression agent; (21) the circSLC22A23 promoting agent is a circSLC22A23 overexpression agent; (22) the circSNHG4 promoting agent is a circSNHG4 overexpression agent; (23) the circTBCD promoting agent is a circTBCD overexpression agent; (24) the circTMEM181 promoting agent is a circTMEM181 overexpression agent; (25) the circUIMC1 promoting agent is a circUIMC1 overexpression agent; and (26) the circVAPB promoting agent is a circVAPB overexpression agent.

The present disclosure provides use of a circRNA having an incomplete double-stranded structure of 16 bp-33 bp in length in preparation or screening of an agent for detecting SLE.

In an embodiment, a circRNA having an incomplete double-stranded structure of 16 bp-33 bp in length serves as a biomarker.

In an embodiment, the agent for detecting SLE is used in determination or diagnosis of SLE.

It needs to be noted that the agent for detecting SLE includes but is not limited to a liquid form.

In an embodiment, the agent for detecting SLE is selected from agents for specifically recognizing circRNAs having an incomplete double-stranded structure of 16 bp-33 bp in length. Specifically, the agent for detecting SLE is one or more selected from the group consisting of: (1) an agent for specifically recognizing circARID1B; (2) an agent for specifically recognizing circCAMSAP1; (3) an agent for specifically recognizing circCCNB1; (4) an agent for specifically recognizing circCNN2; (5) an agent for specifically recognizing circDHX34; (6) an agent for specifically recognizing circEPHB4; (7) an agent for specifically recognizing circEZH2; (8) an agent for specifically recognizing circFCHO2; (9) an agent for specifically recognizing circFGFR1; (10) an agent for specifically recognizing circFKBP8; (11) an agent for specifically recognizing circKIAA0368; (12) an agent for specifically recognizing circMBOAT2; (13) an agent for specifically recognizing circPIP5K1C; (14) an agent for specifically recognizing circPOLR2A; (15) an agent for specifically recognizing circPPP1CB; (16) an agent for specifically recognizing circPROSC; (17) an agent for specifically recognizing circPTK2; (18) an agent for specifically recognizing circPVT1; (19) an agent for specifically recognizing circRELL1; (20) an agent for specifically recognizing circSDHAF2; (21) an agent for specifically recognizing circSLC22A23; (22) an agent for specifically recognizing circSNHG4; (23) an agent for specifically recognizing circTBCD; (24) an agent for specifically recognizing circTMEM181; (25) an agent for specifically recognizing circUIMC1; and (26) an agent for specifically recognizing circVAPB.

In an embodiment, an agent for specifically recognizing a circRNA having an incomplete double-stranded structure of 16 bp-33 bp in length is a primer pair for specifically detecting the circRNA having an incomplete double-stranded structure of 16 bp-33 bp in length. Specifically, (1) the agent for specifically recognizing circARID1B is a primer pair for specifically detecting circARID1B; (2) the agent for specifically recognizing circCAMSAP1 is a primer pair for specifically detecting circCAMSAP 1; (3) the agent for specifically recognizing circCCNB1 is a primer pair for specifically detecting circCCNB1; (4) the agent for specifically recognizing circCNN2 is a primer pair for specifically detecting circCNN2; (5) the agent for specifically recognizing circDHX34 is a primer pair for specifically detecting circDHX34; (6) the agent for specifically recognizing circEPHB4 is a primer pair for specifically detecting circEPHB4; (7) the agent for specifically recognizing circEZH2 is a primer pair for specifically detecting circEZH2; (8) the agent for specifically recognizing circFCHO2 is a primer pair for specifically detecting circFCHO2; (9) the agent for specifically recognizing circFGER1 is a primer pair for specifically detecting circFGER1; (10) the agent for specifically recognizing circFKBP8 is a primer pair for specifically detecting circFKBP8; (11) the agent for specifically recognizing circKIAA0368 is a primer pair for specifically detecting circKIAA0368; (12) the agent for specifically recognizing circMBOAT2 is a primer pair for specifically detecting circMBOAT2; (13) the agent for specifically recognizing circPIP5K1C is a primer pair for specifically detecting circPIP5K1C; (14) the agent for specifically recognizing circPOLR2A is a primer pair for specifically detecting circPOLR2A; (15) the agent for specifically recognizing circPPP1CB is a primer pair for specifically detecting circPPP1CB; (16) the agent for specifically recognizing circPROSC is a primer pair for specifically detecting circPROSC; (17) the agent for specifically recognizing circPTK2 is a primer pair for specifically detecting circPTK2; (18) the agent for specifically recognizing circPVT1 is a primer pair for specifically detecting circPVT1; (19) the agent for specifically recognizing circRELL1 is a primer pair for specifically detecting circRELL1; (20) the agent for specifically recognizing circSDHAF2 is a primer pair for specifically detecting circSDHAF2; (21) the agent for specifically recognizing circSLC22A23 is a primer pair for specifically detecting circSLC22A23; (22) the agent for specifically recognizing circSNHG4 is a primer pair for specifically detecting circSNHG4; (23) the agent for specifically recognizing circTBCD is a primer pair for specifically detecting circTBCD; (24) the agent for specifically recognizing circTMEM181 is a primer pair for specifically detecting circTMEM181; (25) the agent for specifically recognizing circUIMC1 is a primer pair for specifically detecting circUIMC1; and (26) the agent for specifically recognizing circVAPB is a primer pair for specifically detecting circVAPB.

It is first found in studies that the expression of circRNAs having an incomplete double-stranded structure of 16 bp-33 bp in length in PBMCs of SLE patients are significantly lower than in normal subjects.

The present disclosure provides use of an agent for specifically recognizing a circRNA having an incomplete double-stranded structure of 16 bp-33 bp in length in preparation of a kit for detecting SLE.

Specifically, the agent for specifically recognizing a circRNA having an incomplete double-stranded structure of 16 bp-33 bp in length is selected from the group consisting of: (1) an agent for specifically recognizing circARID1B; (2) an agent for specifically recognizing circCAMSAP1; (3) an agent for specifically recognizing circCCNB1; (4) an agent for specifically recognizing circCNN2; (5) an agent for specifically recognizing circDHX34; (6) an agent for specifically recognizing circEPHB4; (7) an agent for specifically recognizing circEZH2; (8) an agent for specifically recognizing circFCHO2; (9) an agent for specifically recognizing circFGER1; (10) an agent for specifically recognizing circFKBP8; (11) an agent for specifically recognizing circKIAA0368; (12) an agent for specifically recognizing circMBOAT2; (13) an agent for specifically recognizing circPIP5K1C; (14) an agent for specifically recognizing circPOLR2A; (15) an agent for specifically recognizing circPPP1CB; (16) an agent for specific recognizing circPROSC; (17) an agent for specifically recognizing circPTK2; (18) an agent for specifically recognizing circPVT1; (19) an agent for specifically recognizing circRELL1; (20) an agent for specifically recognizing circSDHAF2; (21) an agent for specifically recognizing circSLC22A23; (22) an agent for specifically recognizing circSNHG4; (23) an agent for specifically recognizing circTBCD; (24) an agent for specifically recognizing circTMEM181; (25) an agent for specifically recognizing circUIMC1; and (26) an agent for specifically recognizing circVAPB.

A circRNA having an incomplete double-stranded structure of 16 bp-33 bp in length serves as a biomarker.

In an embodiment, the kit for detecting SLE is used in determination or diagnosis of SLE.

It needs to be noted that the agent for specifically recognizing a circRNA having an incomplete double-stranded structure of 16 bp-33 bp in length includes but is not limited to a liquid form.

In an embodiment, an agent for specifically recognizing a circRNA having an incomplete double-stranded structure of 16 bp-33 bp in length is a primer pair for specifically detecting the circRNA having an incomplete double-stranded structure of 16 bp-33 bp in length. Specifically, (1) the agent for specifically recognizing circARID1B is a primer pair for specifically detecting circARID1B; (2) the agent for specifically recognizing circCAMSAP1 is a primer pair for specifically detecting circCAMSAP1; (3) the agent for specifically recognizing circCCNB1 is a primer pair for specifically detecting circCCNB1; (4) the agent for specifically recognizing circCNN2 is a primer pair for specifically detecting circCNN2; (5) the agent for specifically recognizing circDHX34 is a primer pair for specifically detecting circDHX34; (6) the agent for specifically recognizing circEPHB4 is a primer pair for specifically detecting circEPHB4; (7) the agent for specifically recognizing circEZH2 is a primer pair for specifically detecting circEZH2; (8) the agent for specifically recognizing circFCHO2 is a primer pair for specifically detecting circFCHO2; (9) the agent for specifically recognizing circFGER1 is a primer pair for specifically detecting circFGER1; (10) the agent for specifically recognizing circFKBP8 is a primer pair for specifically detecting circFKBP8; (11) the agent for specifically recognizing circKIAA0368 is a primer pair for specifically detecting circKIAA0368; (12) the agent for specifically recognizing circMBOAT2 is a primer pair for specifically detecting circMBOAT2; (13) the agent for specifically recognizing circPIP5K1C is a primer pair for specifically detecting circPIP5K1C; (14) the agent for specifically recognizing circPOLR2A is a primer pair for specifically detecting circPOLR2A; (15) the agent for specifically recognizing circPPP1CB is a primer pair for specifically detecting circPPP1CB; (16) the agent for specifically recognizing circPROSC is a primer pair for specifically detecting circPROSC; (17) the agent for specifically recognizing circPTK2 is a primer pair for specifically detecting circPTK2; (18) the agent for specifically recognizing circPVT1 is a primer pair for specifically detecting circPVT1; (19) the agent for specifically recognizing circRELL1 is a primer pair for specifically detecting circRELL1; (20) the agent for specifically recognizing circSDHAF2 is a primer pair for specifically detecting circSDHAF2; (21) the agent for specifically recognizing circSLC22A23 is a primer pair for specifically detecting circSLC22A23; (22) the agent for specifically recognizing circSNHG4 is a primer pair for specifically detecting circSNHG4; (23) the agent for specifically recognizing circTBCD is a primer pair for specifically detecting circTBCD; (24) the agent for specifically recognizing circTMEM181 is a primer pair for specifically detecting circTMEM181; (25) the agent for specifically recognizing circUIMC1 is a primer pair for specifically detecting circUIMC1; and (26) the agent for specifically recognizing circVAPB is a primer pair for specifically detecting circVAPB.

The present disclosure provides a kit for detecting SLE, which includes an agent for specifically recognizing a circRNA having an incomplete double-stranded structure of 16 bp-33 bp in length.

In an embodiment, a circRNA having an incomplete double-stranded structure of 16 bp-33 bp in length serves as a biomarker.

In an embodiment, the kit for detecting SLE is used in determination or diagnosis of SLE.

It needs to be noted that the agent for specifically recognizing a circRNA having an incomplete double-stranded structure of 16 bp-33 bp in length includes but is not limited to a liquid form.

In an embodiment, an agent for specifically recognizing a circRNA having an incomplete double-stranded structure of 16 bp-33 bp in length is a primer pair for specifically detecting the circRNA having an incomplete double-stranded structure of 16 bp-33 bp in length. Specifically, (1) the agent for specifically recognizing circARID1B is a primer pair for specifically detecting circARID1B; (2) the agent for specifically recognizing circCAMSAP1 is a primer pair for specifically detecting circCAMSAP1; (3) the agent for specifically recognizing circCCNB1 is a primer pair for specifically detecting circCCNB1; (4) the agent for specifically recognizing circCNN2 is a primer pair for specifically detecting circCNN2; (5) the agent for specifically recognizing circDHX34 is a primer pair for specifically detecting circDHX34; (6) the agent for specifically recognizing circEPHB4 is a primer pair for specifically detecting circEPHB4; (7) the agent for specifically recognizing circEZH2 is a primer pair for specifically detecting circEZH2; (8) the agent for specifically recognizing circFCHO2 is a primer pair for specifically detecting circFCHO2; (9) the agent for specifically recognizing circFGER1 is a primer pair for specifically detecting circFGER1; (10) the agent for specifically recognizing circFKBP8 is a primer pair for specifically detecting circFKBP8; (11) the agent for specifically recognizing circKIAA0368 is a primer pair for specifically detecting circKIAA0368; (12) the agent for specifically recognizing circMBOAT2 is a primer pair for specifically detecting circMBOAT2; (13) the agent for specifically recognizing circPIP5K1C is a primer pair for specifically detecting circPIP5K1C; (14) the agent for specifically recognizing circPOLR2A is a primer pair for specifically detecting circPOLR2A; (15) the agent for specifically recognizing circPPP1CB is a primer pair for specifically detecting circPPP1CB; (16) the agent for specifically recognizing circPROSC is a primer pair for specifically detecting circPROSC; (17) the agent for specifically recognizing circPTK2 is a primer pair for specifically detecting circPTK2; (18) the agent for specifically recognizing circPVT1 is a primer pair for specifically detecting circPVT1; (19) the agent for specifically recognizing circRELL 1 is a primer pair for specifically detecting circRELL 1; (20) the agent for specifically recognizing circSDHAF2 is a primer pair for specifically detecting circSDHAF2; (21) the agent for specifically recognizing circSLC22A23 is a primer pair for specifically detecting circSLC22A23; (22) the agent for specifically recognizing circSNHG4 is a primer pair for specifically detecting circSNHG4; (23) the agent for specifically recognizing circTBCD is a primer pair for specifically detecting circTBCD; (24) the agent for specifically recognizing circTMEM181 is a primer pair for specifically detecting circTMEM181; (25) the agent for specifically recognizing circUIMC1 is a primer pair for specifically detecting circUIMC1; and (26) the agent for specifically recognizing circVAPB is a primer pair for specifically detecting circVAPB.

According to the applicant's research findings, the overexpression of the above-mentioned circRNAs having an incomplete double-stranded structure of 16 bp-33 bp in length in model cells, i.e., human HeLa cells, can inhibit the phosphorylation activation of protein kinase PKRs and relevant protein kinases of downstream pathways thereof. However, the overexpression of circSMARCA5, a circRNA without special double-stranded structure, cannot inhibit the posphorylation activation of PKR and relevant protein kinase of downstream pathway thereof. This reveals that the above-mentioned genes of circRNAs having an incomplete double-stranded structure of 16 bp-33 bp in length and expression products thereof may open up a new way to regulate the posphorylation activation of protein PKRs involved in natural immune and relevant protein kinases of downstream pathways thereof in autoimmune diseases.

According to the applicant's research findings, the expression of the above-mentioned genes of circRNAs having an incomplete double-stranded structure of 16 bp-33 bp in length is significantly downregulated in PBMCs of SLE patients. The overexpression of circRNAs having an incomplete double-stranded structure of 16 bp-33 bp in length in primary cells or immune cell T cells can inhibit the posphorylation activation of protein kinase PKRs and the expression of cytokine IFN-beta and diagnostic genes for SLE. This reveals that the genes of circRNAs having an incomplete double-stranded structure of 16 bp-33 bp in length and the expression products thereof may open up a new way to diagnose and treat SLE.

The characteristics and effects of the circRNAs having a special structure will be explained below by taking circPOLR2A for example Example 1

Position Map of circPOLR2A on a Chromosome

The position of circPOLR2A on a chromosome was as shown in FIG. 1. Its sequence was obtained from circexplorer database (yanglab.github.io/CIRCexplorer/). The gene sequence of circPOLR2A was shown in SEQ ID NO: 1. The agent for detecting the circRNA molecular marker for SLE was a pair of specific primers, including an upstream primer: aatcggcctgtcatgggtat (SEQ ID NO: 2), and downstream primer: aaagtctgcattgtacggagt (SEQ ID NO: 3). The pair of primers was designed by studying and analyzing circularization sites of these circRNAs. The primers were synthesized by Shanghai Biosune Co., LTD.

Example 2

Detection of the Expression of circPOLR2A in SLE Patients by Using Specific Detection Primers Step 1: PBMCs were Obtained from Normal Individuals and SLE Patients.

Peripheral blood samples were collected from 32 normal individuals and 32 SLE patients in Shanghai Renji Hospital. Isolated PBMCs were obtained by using a density gradient centrifugation method for subsequent detection.

Step 2: RNAs Extraction

The culture medium was removed firstly. Cells were washed twice with PBS and the liquid was removed by aspiration. Cells were placed on ice and added with Trizol agent (1 ml added to a 10 cm culture dish; 0.5 ml added to a 6 cm culture dish; 0.2 ml added to each well of a 6-well plate). As liquid became viscous, cells were detached and fully blowed until the liquid was clear. The cell lysate was pipetted into a DEPC treated EP tube, and 0.2 times the volume of chloroform was added thereto. The EP tube was shaken for 15 seconds, inverted several times, and allowed to stand at room temperature for 2-3 minutes. After centrifugation at 12000 g at 4° C. for 15 minutes, the liquid was divided into a bottom layer (red phenol-chloroform phase), a middle layer (pink junction phase) and an upper layer (colorless liquid phase including all RNAs therein). The supernatant was carefully transferred to a new EP tube, ensuring that no middle layer was aspirated, and an equal volume of isopropanol was added thereto. The EP tube was inverted several times and allowed to stand at room temperature for 10 minutes. After centrifugation at 12000 g at 4° C. for 15 minutes, the supernatant was removed, with small milk-white precipitate left at the bottom of the EP tube, i.e., RNAs. The precipitate was washed twice with 1 ml of 75% DEPC-ethanol. The supernatant was removed by aspiration, followed by air-drying for 10 minutes. 20-30 μl of DEPC treated water was added to the precipitate and mixed well such that the RNAs were dissolved. Concentrations were measured as follows: A260/280, in a range of 1.8-2.0; A260/230, about 2.0; and A260, in a range of 0.1-1. The samples were stored at −80° C.

Step 3: cDNAs were Obtained by Reverse Transcription.

(1) RNAs were treated with DNase. The reaction system was shown below:

| | |
|---|---|
| RNA | 1~5 μg |
| DEPC-treated water | |
| RQ1 DNase 10 × Reaction Buffer | 1 μl |
| RQ1 RNase-Free DNase | 1 U/μgRNA |

After reaction at 37° C. for 30 minutes, 1 μl stop Buffer was added, followed by reaction at 65° C. for 10 minutes.

(2) Each reaction system, to which 0.5 μg of random primers was added, was allowed to react at 72° C. for 5 minutes, and then placed on ice for 2 minutes.

(3) The reaction system of reverse transcription was shown below:

| | |
|---|---|
| 5 × Reverse Transcription Buffer | 5 μl |
| dNTP (10 mM) | 1.25 μl |
| RNase Inhibitor | 0.5 μl |
| MML-V Reverse Transcripase | 1 μl |
| DEPC-treated water | 5.25 μl |

The reaction system was allowed to react at 37° C. for 60 minutes and react at 72° C. for 10 minutes.

Step 4: Fluorescent Quantitative Q-PCR

Real-time quantitative PCR reaction was completed in Biorad realtime PCR instrument. The reaction system was shown below:

| | |
|---|---|
| 2 × SYBR Green Taq mix | 10 μl |
| Primer (F + R) | 1 μl |
| Template | 1 μl |
| ddH$_2$O | 8 μl |

Reaction conditions were as follows:

| | | |
|---|---|---|
| Stage 1: | 95° C., 30 s | |
| Stage 2: | 95° C., 10 s | |
| | 60° C., 15 s | 40 cycle |
| | 72° C., 30 s | |

Stage 3L Melting Curve

Data was analyzed according to $2^{-\Delta \neq CT}$ method (Kenneth J. Livak, Thomas D. Schmittgen. Method, 25, 2001: 402-408).

Figure 2:
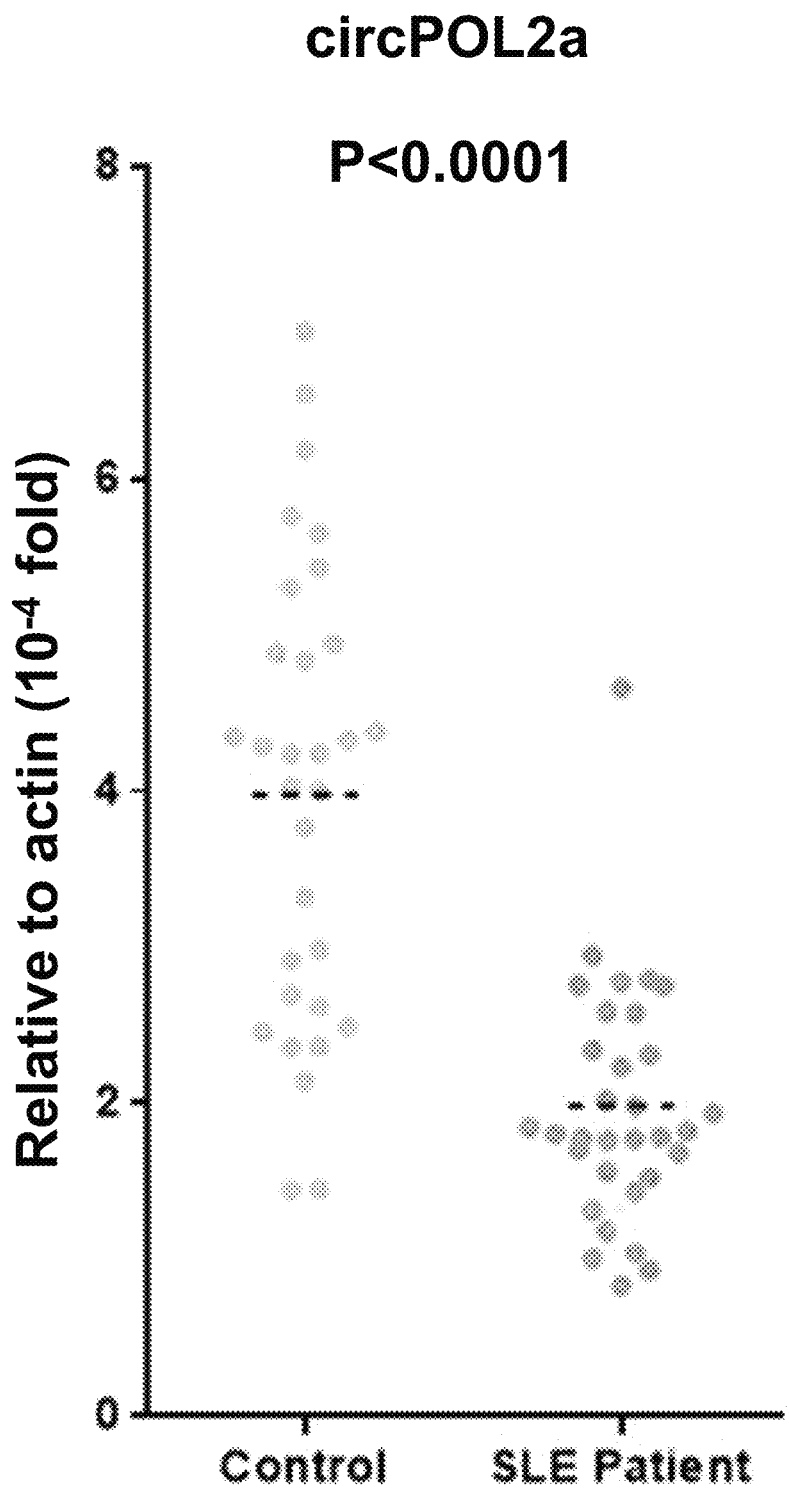
FIG. 2 illustrates the expression of circPOLR2A in SLE patients detected with specific detection primers.
Figure 3:
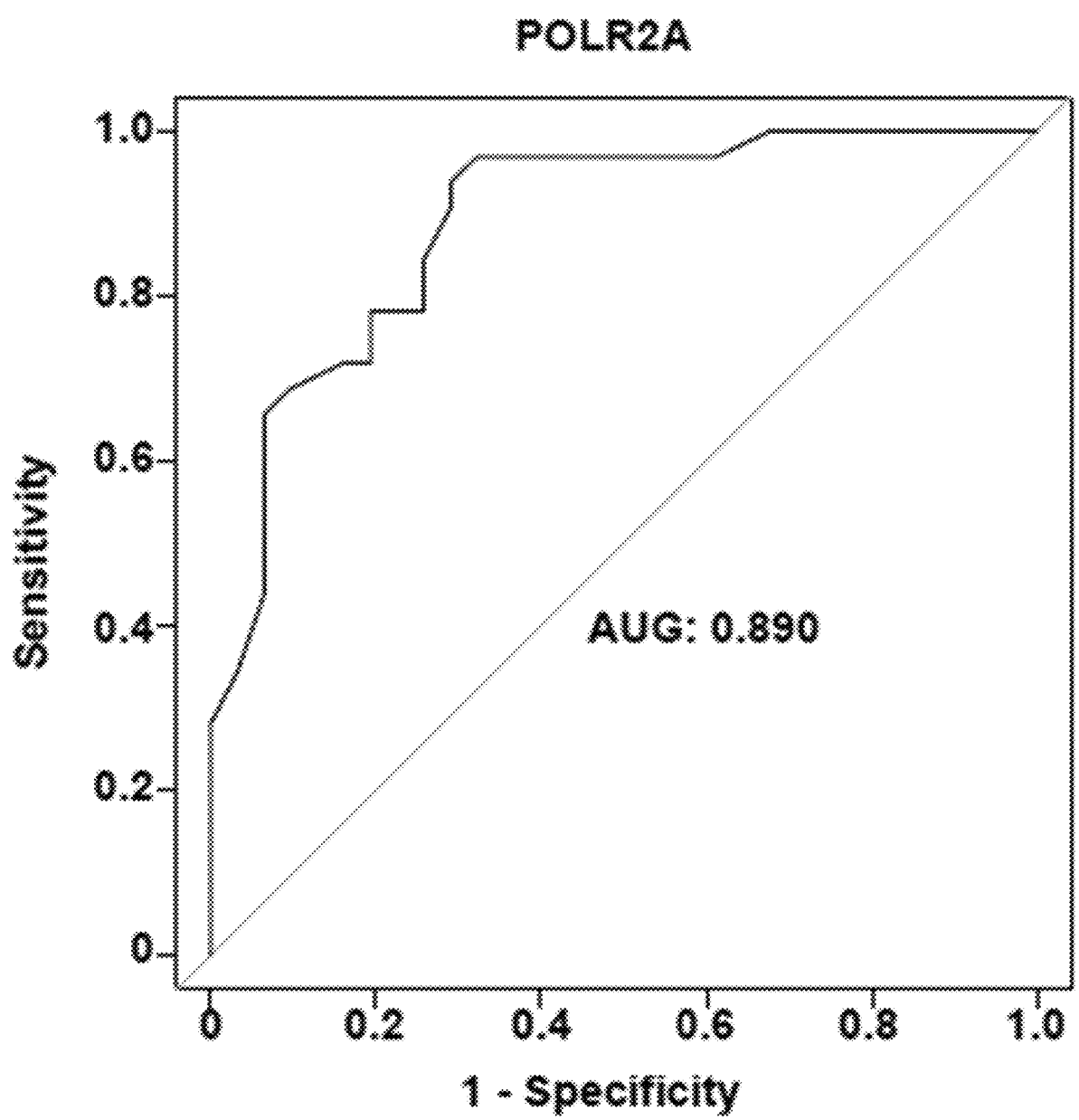
FIG. 3 illustrates a receiver operating characteristic (ROC) curve obtained with circRNA circPOLR2A.

As shown from FIG. 2, the expression of the circRNA circPOLR2A in PBMCs of SLE patients was significantly lower than in normal individuals. Independent-samples t-test was conducted, where the P value of the circRNA circPOLR2A was lower than 0.05, demonstrating a significant difference. As shown in FIG. 3, a receiver operating characteristic (ROC) curve was plotted with the circRNA circPOLR2A, where the area under the curve (AUC) was above 0.89, indicating that this circRNA, as a marker, had extremely high diagnostic sensitivity and diagnostic specificity for identification of SLE by using PBMC samples.

Example 3

Schematic Diagram of Secondary Structures of circPOLR2A, 26 circRNAs of a Same Type having a Special Double-Stranded Structure and circRNA circSMARCA5 having No Special Double-Stranded Structure Step 1: Human-Derived Model Research Cell, i.e., PA-1 Ovarian Cancer Cell Line was Obtained.

Step 2: RNAs were Labeled and Extracted.

The culture medium was removed firstly. Cells were washed twice with PBS and added with SHAPE reaction labeling compound NAI to label RNAs. After labeling for 10 minutes, the liquid was removed by aspiration. Cells were placed on ice and added with Trizol agent (1 ml added to a 10 cm culture dish; 0.5 ml added to a 6 cm culture dish; 0.2 ml added to each well of a 6-well plate). As liquid became viscous, cells were detached and fully blowed until the liquid was clear. The cell lysate was pipetted into a DEPC treated EP tube, and 0.2 times the volume of chloroform was added thereto. The EP tube was shaken for 15 seconds, inverted several times, and allowed to stand at room temperature for 2-3 minutes. After centrifugation at 12000 g at 4° C. for 15 minutes, the liquid was divided into a bottom layer (red phenol-chloroform phase), a middle layer (pink junction phase) and an upper layer (colorless liquid phase including all RNAs therein). The supernatant was carefully transferred to a new EP tube, ensuring that no middle layer was aspirated, and an equal volume of isopropanol was added thereto. The EP tube was inverted several times and allowed to stand at room temperature for 10 minutes. After centrifugation at 12000 g at 4° C. for 15 minutes, the supernatant was removed, with small milk-white precipitate left at the bottom of the EP tube, i.e., RNAs. The precipitate was washed twice with 1 ml of 75% DEPC-ethanol. The supernatant was removed by aspiration, followed by air-drying for 10 minutes. 20-30 μl of DEPC treated water was added to the precipitate and mixed well such that the RNAs were dissolved. Concentrations were measured as follows: A260/280, in a range of 1.8-2.0; A260/230, about 2.0; and A260, in a range of 0.1-1. The samples were stored at −80° C.

Step 3: cDNAs were Obtained by Reverse Transcription.
(1) RNAs were treated with DNase. The reaction system was shown below:

| | |
|---|---|
| RNA | 1~5 μg |
| DEPC-treated water | |
| RQ1 DNase 10 × Reaction Buffer | 1 μl |
| RQ1 RNase-Free DNase | 1 U/μgRNA |

After reaction at 37° C. for 30 minutes, 1 μl stop Buffer was added, followed by reaction at 65° C. for 10 minutes.
(2) Each reaction system, to which 0.5 μg of specific primer was added, was allowed to react at 72° C. for 5 minutes, and then placed on ice for 2 minutes.
(3) The reaction system of reverse transcription was shown below:

| | |
|---|---|
| 5 × Reverse Transcription Buffer | 5 μl |
| dNTP (10 mM) | 1.25 μl |
| RNase Inhibitor | 0.5 μl |
| MML-V Reverse Transcripase | 1 μl |
| DEPC-treated water | 5.25 μl |

Figure 4:
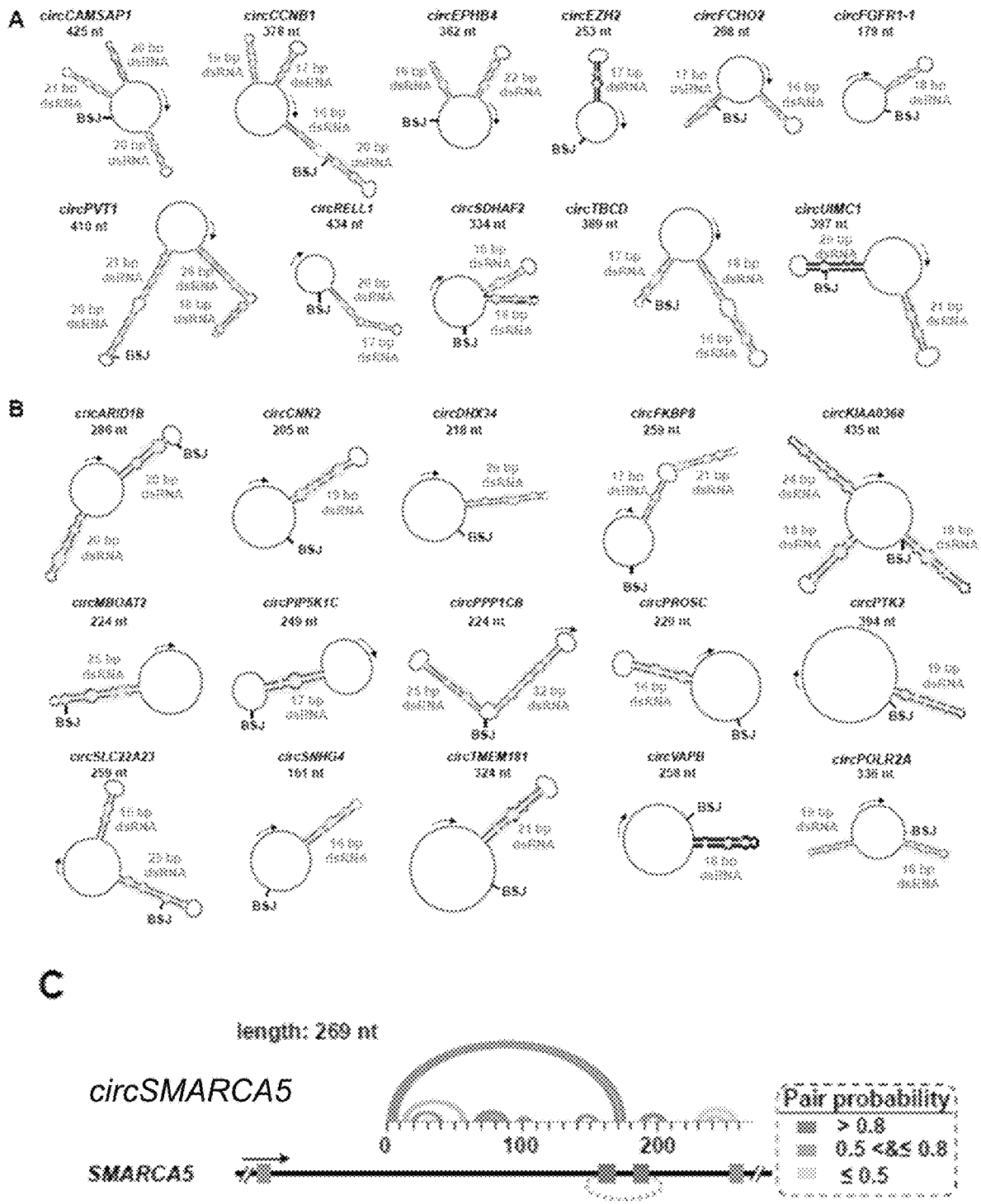
FIG. 4 illustrates secondary structure diagrams of circPOLR2A and 26 circRNAs of a same type having a special double-stranded structure and circRNA circSMARCA5 having no special double-stranded structure.

The reaction system was allowed to react at 37° C. for 60 minutes and react at 42° C. for 180 minutes. The reverse transcription products were subjected to high-throughput sequencing RNA-Seq analysis, and the secondary structures of corresponding RNAs were identified. Secondary structure maps of 27 circRNAs were plotted. FIG. 4 illustrates 26 circRNAs having a special double-stranded structure and one circRNA circSMARCA5 without special double-stranded structure.

Example 4

Construction of pZW1-circPOLR2A Vector (Zhang et al., Cell, 2014)

The loop region of circPOLR2A was obtained by using PCR method. The linear complete sequence was inserted into pZW1 vector via multiple cloning sites. The recombinant plasmid was identified by Sanger sequencing, with empty pZW1 vector in which the sequence was not inserted as negative control. The constructed pZW1-circPOL2A vector had a sequence of SEQ ID NO: 4, which was specifically as follows:

tggaagggctaattcactcccaaagaagacaagatatcctgatctgtggatctaccacacacaaggctacttccctgattagcagaac
tacacaccagggccaggggtcagatatccactgacctttggatggtgctacaagctagtaccagttgagccagataaggtagaagaggcca
ataaaggagagaacaccagcttgttacaccctgtgagcctgcatgggatggatgacccggagagagaagtgttagagtggaggtttgacag
ccgcctagcatttcatcacgtggcccgagagctgcatccggagtacttcaagaactgctgatatcgagcttgctacaagggacttttccgctgg
ggactttccagggaggcgtggcctgggcgggactggggagtggcgagccctcagatcctgcatataagcagctgctattttttgcctgtactggg
tctctctggttagaccagatctgagcctgggagctctctggctaactagggaacccactgcttaagcctcaataaaagcttgccttgagtgcttca
agtagtgtgtgcccgtctgttgtgtgactctggtaactagagatccctcagacccttttagtcagtgtggaaaatctctagcagtggcgcccgaa
cagggacttgaaagcgaaagggaaaccagaggagctctctcgacgcaggactcggcttgctgaagcgcgcacggcaagaggcgaggg
gcggcgactggtgagtacgccaaaaattttgactagcggaggctagaaggagagagatgggtgcgagagcgtcagtattaagcggggga
gaattagatcgcgatgggaaaaaattcggttaaggccagggggaaagaaaaaatataaattaaaacatatagtatgggcaagcagggagct
agaacgattcgcagttaatcctggcctgttagaaacatcagaaggctgtagacaaatactgggacagctacaaccatcccttcagacaggatc
agaagaacttagatcattatataatacagtagcaaccctctattgtgtgcatcaaaggatagagataaaagacaccaaggaagctttagacaag
atagaggaagagcaaaacaaaagtaagaccaccgcacagcaagcggccggccgctgatcttcagacctggaggaggagatatgaggga
caattggagaagtgaattatataaatataaagtagtaaaaattgaaccattaggagtagcacccaccaaggcaaagagaagagtggtgcaga
gagaaaaaagagcagtgggaataggagatttgttccttgggttcttgggagcagcaggaagcactatgggcgcagcgtcaatgacgctgac
ggtacaggccagacaattattgtctggtatagtgcagcagcagaacaatttgctgagggctattgaggcgcaacagcatctgttgcaactcac
agtctggggcatcaagcagaccaggcaagaatcctggctgtggaaagatacctaaaggatcaacagctcctggggatttggggttgctctg
gaaaactcatttgcaccactgctgtgccttggaatgctagttggagtaataaatctctggaacagatttggaatcacacgacctggatggagtg
ggacagagaaattaacaattacacaagcttaatacactccttaattgaagaatcgcaaaaccagcaagaaaagaatgaacaagaattattgga
attagataaatgggcaagtttgtggaattggtttaacataacaaattggctgtggtatataaaattattcataatgatagtaggaggcttggtaggtt
taagaatagtttttgctgtactttctatagtgaatagagttaggcagggatattcaccattatcgtttcagacccacctcccaaccccgagggggac
ccgacaggcccgaaggaatagaagaagaaggtggagagagagacagagacagatccattcgattagtgaacggatctcgacggtatcgc
cgaattcacaaatggcagtattcatccacaatttttaaaagaaaaggggggattgggggtacagtgcaggggaaagaatagtagacataata
gcaacagacatacaaactaaagaattacaaaaacaaattacaaaaattcaaaattttcgggtttattacagggacagcagagatccagtttgga
ctagtcgtgaggctccggtgcccgtcagtgggcagagcgcacatcgcccacagtccccgagaagttgggggggaggggtcggcaattgaa
ccggtgcctagagaaggtggcgcggggtaaactgggaaagtgatgtcgtgtactggctccgcctttttcccgagggtgggggagaaccgta
tataagtgcagtagtcgccgtgaacgttcttttttcgcaacgggtttgccgccagaacacaggtaagtgccgtgtgtggttcccgcgggcctgg
cctctttacggggttatggcccttgcgtgccttgaattacttccacgcccctggctgcagtacgtgattcttgatcccgagcttcgggttggaagtg
ggtgggagagttcgaggccttgcgcttaaggagccccttcgcctcgtgcttgagttgaggcctggcctgggcgctggggccgccgcgtgcg
aatctggtggcaccttcgcgcctgtctcgctgctttcgataagtctctagccatttaaaattttgatgacctgctgcgacgcattttttttctggcaaga
tagtcttgtaaatgcgggccaagatctgcacactggtatttcggtttttggggccgcggggcggcgacggggcccgtgcgtcccagcgcacat
gttcggcgaggcggggcctgcgagcgcggccaccgagaatcggacgggggtagtctcaagctggccggcctgctctggtgcctggcctc
gcgccgccgtgtatcgccccgccctgggcggcaaggctggcccggtcggcaccagttgcgtgagcggaaagatggccgcttcccggccc
tgctgcagggagctcaaaatggaggacgcggcgctcgggagagcgggcgggtgagtcacccacacaaaggaaaagggcctttccgtcct
cagccgtcgcttcatgtgactccacggagtaccgggcgccgtccaggcacctcgattagttctcgagcttttggagtacgtcgtctttaggttg
gggggaggggttttatgcgatggagtttccccacactgagtgggtggagactgaagttaggccagcttggcacttgatgtaattctccaggaa
tttgcccttttttgagtttggatcttggacattctcaagcctcagacagtggttcaaagttttttttcttccatttcaggtgtcgtgaagcggccgcaccg
gtctgcagctagctcgagtctagaATGGTGAGCAAGGGCGAGGAGCTGTTCACCGGGGTGGTGCCC
ATCCTGGTCGAGCTGGACGGCGACGTAAACGGCCACAAGTTCAGCGTGTCCGGCGAG
GGCGAGGGCGATGCCACCTACGGCAAGCTGACCCTGAAGTTCATCTGCACCACCGGC
AAGCTGCCCGTGCCCTGGCCCACCCTCGTGACCACCCTGACCTACGGCGTGCAGTGCT

```
TCAGCCGCTACCCCGACCACATGAAGCAGCACGACTTCTTCAAGTCCGCCATGCCCGA

AGGCTACGTCCAGGCACGTAGCAGGCCAGGGCCTCTCTCAGCCACCTGAGCAGAAAG

CTTTCCAAGATAGGGCAGGCTGGGTTAGGCCATCTGAGTCTGTCTCGTTCATTGGGATC

CAGACTTGACTGTCTTGTTAAAGGCTGTTGCTGCCCAGGTGTGCAGGGAGCTGTTGGT

CTCTGGCATTCAGGGTGGGGGTGGTATAAACCCGGGGCAGCTTGCATATGGCAGGGAA

GAGGGATCCGTGGAGGAACAGTGCAGAAGGCTTTATGTTCAGAATCTCTCTTGCTTTT

CTTCTAGACTGAGTTCCTTGAGATTGGTGAATGCTGTGTATTATTCATCCCTGATAACCT

GGTGTTTGGCCCAGGGCCTTGTCCAGAGGAGTGTTTGATAAGTGTTTCAAGTGAATTA

GCACCACGATGTCATCTCTTTTCAGTTTACAAAGGACggacacccctgacccggtctcagaaagcctga aagcagaattagtcattagaagggtggttggcttggtcggcatagactttgagcagaaagaggttgaaaatgttgagcctgatttctcttaggcc cctctgcagtgtctgttgtggaggccagatacgtaactgcttccgcttttttggtctcattcaaggtgagcaaatccccttcatgtttctcaccaga caatgcagctgatgaggttccagctttgcaaatgtagtcatccatgaggactgtcttcctgagatttcatcaggCTCGAGGGACTTG

CAAAGGACTTTAGGTCCATTGTCCTTTTATTCTTAGATACCTCTTTCACTGAGACCTTTT

CCTTACCTCACCTCTCTAGGTGGAACGGCACATGTGTGATGGGGACATTGTTATCTTCA

ACCGGCAGCCAACTCTGCACAAAATGTCCATGATGGGGCATCGGGTCCGCATTCTCCC

ATGGTCTACCTTTCGCTTGAATCTTAGGTCAGTCCCTGGCTGAGGGAAGCAGGCTGGA

ATTGGTGGGAGGCGGGCAGGCTGGGTGGCTCCTCAAGGTTTCGCTGCAGACATCTTCC

CAACCCTGACTTTTCTCTTTAACTGTAGTGTGACAACTCCGTACAATGCAGACTTTGAC

GGGGATGAGATGAACTTGCACCTGCCACAGTCTCTGGAGACGCGAGCAGAGATCCAG

GAGCTGGCCATGGTTCCTCGCATGATTGTCACCCCCCAGAGCAATCGGCCTGTCATGG

GTATTGTGCAGGACACACTCACAGCAGTGCGCAAATTCACCAAGAGAGACGTCTTCCT

GGAGCGGGTGTGTGGTCCAAATGGAAACCTGGCTTAAGTGGGCAGTGGGGCTCTGGG

GTGCAAGGTGGAGGCTAGAGAGGAAGAGCTGTGTTTTTTTCCTGACTTACCCAGCA

GTGGTCTGTGAGATTGTCTTTTCTGGTGGGCGAACAAAAAGGGGGTTAGGAAAACTC

AGGCCAAAAAAGTGTAAGGCGTTAATTCCCCATTTAATTCCTTAAAATTTCATGTAATA

CCAGGTATTGCCTGTAAAGGAAAGATAAAGGGAAAAATAAGTAAGACCTTGTTAAAAT

TTTATTTTTCTATTTTAACCTTCACTTATTTCCTAATTATTAAAAGAAATTTATGCTTATTG

TTAAGAACAAAAAAATTTCAGTATTACAATGAATTTTTAATTAAAAGTTTTTGGcctgatgaa atctcaggaagacagtcctcatggatgactacatttgcaaagctggaacctcatcagctgcattgtctggtgagaaacatgaagggatttgct caccttgaatgagaccaaaaaaagcggaagcagttacgtatctggcctccacaacagacactgcagaggggcctaagagaaatcaggctc aacattttcaacctctttctgctcaaagtctatgccgaccaagccaaccaccccttctaatgactaattctgctttcaggctttctgagaccgggtca gggggtgtccTTAAAGGTTGGAAAAAACTTTTCCTGTCATCTTTGCCTCCAAAATCTGGCTT

TCTCCCTTGGGCAGGGAAACCTCCCCAACATTTCTCTATCATCCCTGAGATGTGGGGCC

TGCACTCTGACTTCTGTCTGCCTTACTCTTTGTCTTACAGGAGCGCACCATCTTCTTCA

AGGACGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCTGGGG

CACAAGCTGGAGTACAACTACAACAGCCACAACGTCTATATCATGGCCGACAAGCAG

AAGAACGGCATCAAGGTGAACTTCAAGATCCGCCACAACATCGAGGACGGCAGCGTG

CAGCTCGCCGACCACTACCAGCAGAACACCCCCATCGGCGACGGCCCCGTGCTGCTG

CCCGACAACCACTACCTGAGCACCCAGTCCGCCCTGAGCAAAGACCCCAACGAGAAG
```

-continued

```
CGCGATCACATGGTCCTGCTGGAGTTCGTGACCGCCGCCGGGATCACTCTCGGCATGG

ACGAGCTGTACAAGTAAggatccctccccccccctaacgttactggccgaagccgcttggaataaggccggtgtgcgtttg tctatatgttattttccaccatattgccgtcttttggcaatgtgagggcccggaaacctggccctgtcttcttgacgagcattcctaggggtctttcc cctctcgccaaaggaatgcaaggtctgttgaatgtcgtgaaggaagcagttcctctggaagcttcttgaagacaaacaacgtctgtagcgacc ctttgcaggcagcggaaccccccacctggcgacaggtgcctctgcggccaaaagccacgtgtataagatacacctgcaaaggcggcacaa ccccagtgccacgttgtgagttggatagagtggaaagagtcaaatggctctcctcaagcgtattcaacaaggggctgaaggatgcccagaa ggtaccccattgtatgggatctgatctggggcctcggtgcacatgctttacatgtttagtcgaggttaaaaaaacgtctaggccccccgaac cacggggacgtggttttctttgaaaaacacgatgataatatggccacacatatggcccagtccaagcacggcctgaccaaggagatgacca tgaagtaccgcatggagggctgcgtggacggccacaagttcgtgatcaccggcgagggcatcggctaccccttcaagggcaagcaggcc atcaacctgtgcgtggtggagggcggccccttgcccttcgccgaggacatcttgtccgccgccttcatgtacggcaaccgcgtgttcaccga gtaccccaggacatcgtcgactacttcaagaactcctgccccgccggctacacctgggaccgctccttcctgttcgaggacggcgccgtgt gcatctgcaacgccgacatcaccgtgagcgtggaggagaactgcatgtaccacgagtccaagttctacggcgtgaacttccccgccgacgg ccccgtgatgaagaagatgaccgacaactgggagccctcctgcgagaagatcatccccgtgcccaagcagggcatcttgaagggcgacgt gagcatgtacctgctgctgaaggacggtggccgcttgcgctgccagttcgacaccgtgtacaaggccaagtccgtgccccgcaagatgccc gactggcacttcatccagcacaagctgacccgcgaggaccgcagcgacgccaagaaccagaagtggcacctgaccgagcacgccatcg cctccggctccgccttgccctgaatcgatagatcctaatcaacctctggattacaaaatttgtgaaagattgactggtattcttaactatgttgctcc ttttacgctatgtggatacgctgctttaatgcctttgtatcatgctattgcttcccgtatggctttcattttctcctccttgtataaatcctggttgctgtct cttatgaggagttgtggcccgttgtcaggcaacgtggcgtggtgtgcactgtgtttgctgacgcaacccccactggagggcattgccaca cctgtcagctcctttccgggacttcgctttcccctccctattgccacggcggaactcatcgccgcctgccttgcccgctgctggacaggggc tcggctgttgggcactgacaattccgtggtgttgtcgggaaatcatcgtcctttccttggctgctcgcctgtgttgccacctggattctgcgcgg gacgtccttctgctacgtcccttcggccctcaatccagcggaccttccttcccgcggcctgctgccggctctgcggcctcttccgcgtctcgc cacgccctcagacgagtcggatctccctttgggccgcctccccgcctgagatcctttaagaccaatgacttacaaggcagctgtagatcttag ccacttttttaaaagaaaagggggggactggaagggctaattcactcccaacgaagacaagatctgcttttttgcttgtactgggtctctctggttag accagatctgagcctgggagactctggctaactagggaacccactgcttaagcctcaataaagcttgccttgagtgcttcaagtagtgtgtgc ccgtctgttgtgtgactctggtaactagagatccctcagaccctttttagtcagtgtggaaaatctctagcagtagtagttcatgtcatcttattattca gtatttataacttgcaaagaaatgaatatcagagagtgagaggcccgggttaattaaggaaagggctagatcattcttgaagacgaaagggcc tcgtgatacgcctatttttataggttaatgtcatgataataatggtttcttagacgtcaggtggcacttttcggggaaatgtgcgcggaaccccctatt tgtttatttttctaaatacattcaaatatgtatccgctcatgagacaataaccctgataaatgcttttcaataatattgaaaaaggaagagtatgagtatt caacatttccgtgtcgcccttattcccttttttgcggcattttgccttcctgttttgctcacccagaaacgctggtgaaagtaaaagatgctgaagat cagttgggtgcacgagtgggttacatcgaactggatctcaacagcggtaagatccttgagagttttcgccccgaagaacgttttccaatgatga gcacttttaaagttctgctatgtggcgcggtattatcccgtgttgacgccgggcaagagcaactcggtcgccgcatacactattctcagaatgac ttggttgagtactcaccagtcacagaaaagcatcttacggatggcatgacagtaagagaattatgcagtgctgccataaccatgagtgataaca ctgcggccaacttacttctgacaacgatcggaggaccgaaggagctaaccgcttttttgcacaacatgggggatcatgtaactcgccttgatc gttgggaaccggagctgaatgaagccataccaaacgacgagcgtgacaccacgatgcctgtagcaatggcaacaacgttgcgcaaactatt aactggcgaactacttactctagcttcccggcaacaattaatagactggatggaggcggataaagttgcaggaccacttctgcgctcggcccttc cggctggctggtttattgctgataaatctggagccggtgagcgtgggtctcgcggtatcattgcagcactggggccagatggtaagccctcc cgtatcgtagttatctacacgacggggagtcaggcaactatggatgaacgaaatagacagatcgctgagataggtgcctcactgattaagcat tggtaactgtcagaccaagtttactcatatatactttagattgatttaaaacttcttttttaatttaaaaggatctaggtgaagatcctttttgataatctc atgaccaaaatcccttaacgtgagttttcgttccactgagcgtcagaccccgtagaaaagatcaaaggatcttcttgagatcctttttttctgcgcg taatctgctgcttgcaaacaaaaaaaccaccgctaccagcggtggtttgtttgccggatcaagagctaccaactcttttccgaaggtaactggc ttcagcagagcgcagataccaaatactgttcttctagtgtagccgtagttaggccaccacttcaagaactctgtagcaccgcctacatacctcgc
```

-continued

```
tctgctaatcctgttaccagtggctgctgccagtggcgataagtcgtgtcttaccggggttggactcaagacgatagttaccggataaggcgcag cggtcgggctgaacggggggttcgtgcacacagcccagcttggagcgaacgacctacaccgaactgagatacctacagcgtgagctatga gaaagcgccacgcttcccgaagggagaaaggcggacaggtatccggtaagcggcagggtcggaacaggagagcgcacgagggagctt ccaggggaaacgcctggtatctttatagtcctgtcgggtttcgccacctctgacttgagcgtcgattttttgtgatgctcgtcaggggggcgga gcctatggaaaaacgccagcaacgcggccttttttacggttcctggccttttgctggccttttgctcacatgttcttttcctgcgttatcccctgattct gtggataaccgtattaccgcctttgagtgagctgataccgctcgccgagcgaacgaccgagcgcagcgagtcagtgagcgaggaagcg gaagagcgcccaatacgcaaaccgcctctccccgcgcgttggccgattcattaatgcagcaagctcatggctgactaatttttttattatgca gaggccgaggccgcctcggcctctgagctattccagaagtagtgaggaggcttttttggaggcctaggcttttgcaaaaagctccccgtggc acgacaggtttcccgactggaaagcgggcagtgagcgcaacgcaattaatgtgagttagctcactcattaggcacccaggctttacactttat gcttccggctcgtatgttgtggaattgtgagcggataacaatttcacacaggaaacagctatgacatgattacgaatttcacaaataaagcatt tttttcactgcattctagttgtggtttgtccaaactcatcaatgtatcttatcatgtctggatcaactggataactcaagctaaccaaaatcatcccaa acttccacccctatacctattaccactgccaattacctgtggtttcatttactctaaacctgtgattcctctgaattattttcattttaaagaaattgtat ttgttaaatatgtactacaaacttagtagt.
```

Example 5

Detection of Phosphorylation Levels of PKR and Downstream Genes of PKR after the Overexpression of circPOLR2A and circRNA circSMARCA5 without Special Double-Stranded Structure The pZW1-circPOLR2A and pZW1-circSMARCA5 expression vectors prepared in Example 4 were introduced into human HeLa cells by Lipo2000 Transfection method to overexpress circPOLR2A and circSMARCA5. After 12-14 hours, a stimulating compound poly(I:C), a mimic of viral double-stranded RNA, was added, and cells were collected at corresponding time points for Western Blot detection and Q-PCR detection.

Figure 5:
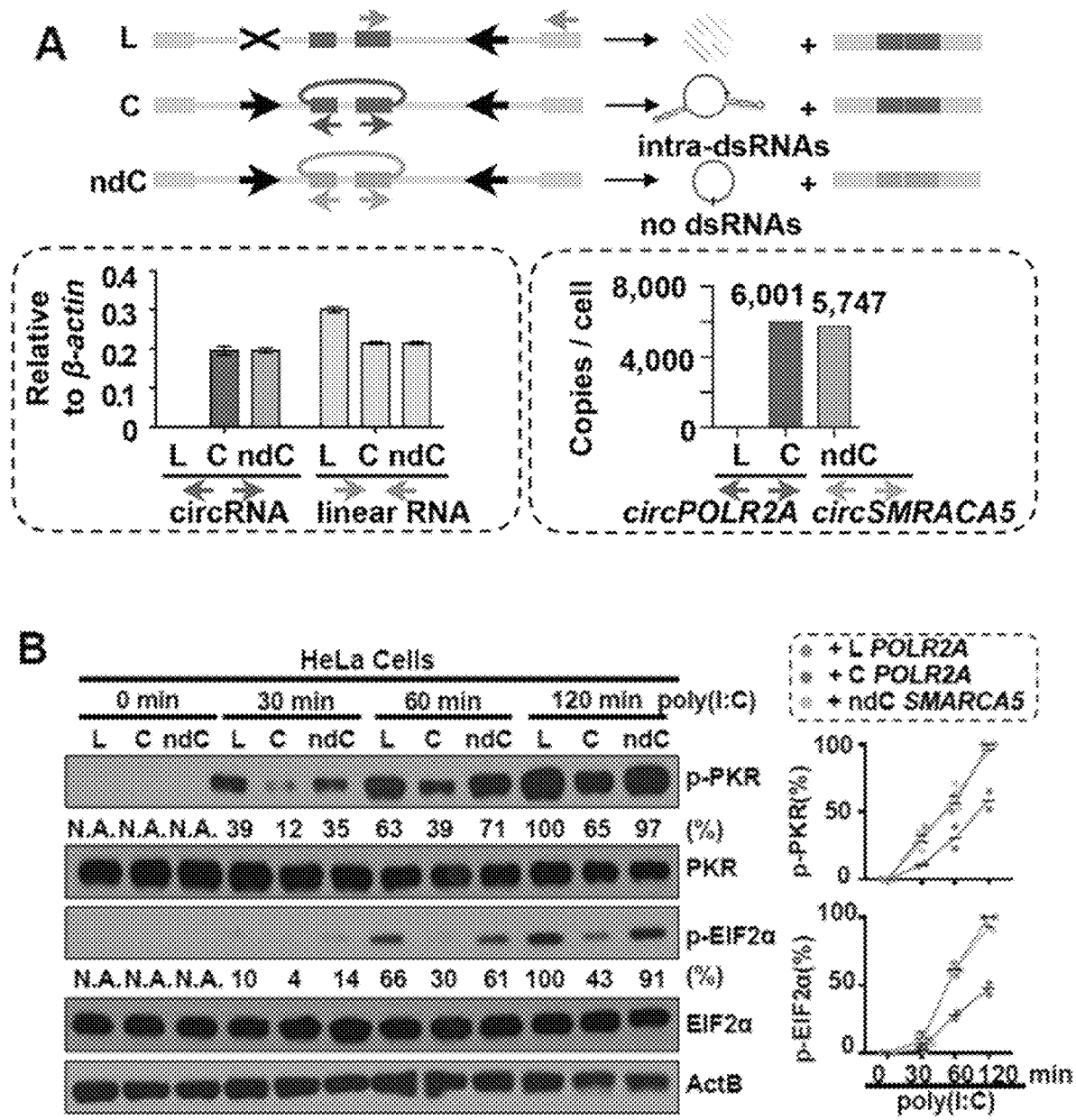
FIG. 5 illustrates phosphorylation levels of PKR and downstream genes of PKR detected after the overexpression of circPOLR2A and circRNA circSMARCA5 having no special double-stranded structure.

As shown in FIG. 5, after the overexpression of circPOLR2A, the PKR phosphorylation level and the phosphorylation level of downstream genes of PKR in HeLa cells were significantly decreased when the stimulating compound [poly(I:C)] (a mimic of viral double-stranded RNA) was added for innate immune stimulation. After the overexpression of circSMARCA5, the PKR phosphorylation level and the phosphorylation level of downstream genes of PKR in HeLa cells showed no significant change when the stimulating compound [poly(I:C)] (a mimic of viral double-stranded RNA) was added for innate immune stimulation.

circPOLR2A and 25 circRNAs of the same type all had such a special double-stranded structure. The above experimental results fully showed that overexpression of circPOLR2A and the genes of 25 circRNAs of the same type having a special double-stranded structure and expression products thereof could be used to regulate the phosphorylation level of protein PKR involved in innate immune pathways and the phosphorylation level of downstream genes of PKR.

Example 6

Detection of Phosphorylation Level of PKR and Expression of Cytokine IFN-Beta and Diagnostic Genes MX-1, LY-6E and IFIT3 for SLE after the Overexpression of circPOLR2A PBMCs of SLE patients were isolated by using a density gradient centrifugation method. The pZW1-circPOLR2A prepared in Example 4 was introduced to the primary cells by using an electroporation transfection method to overexpress circPOLR2A. After 12-14 hours, cells were collected for Western Blot detection and Q-PCR detection.

Figure 6:
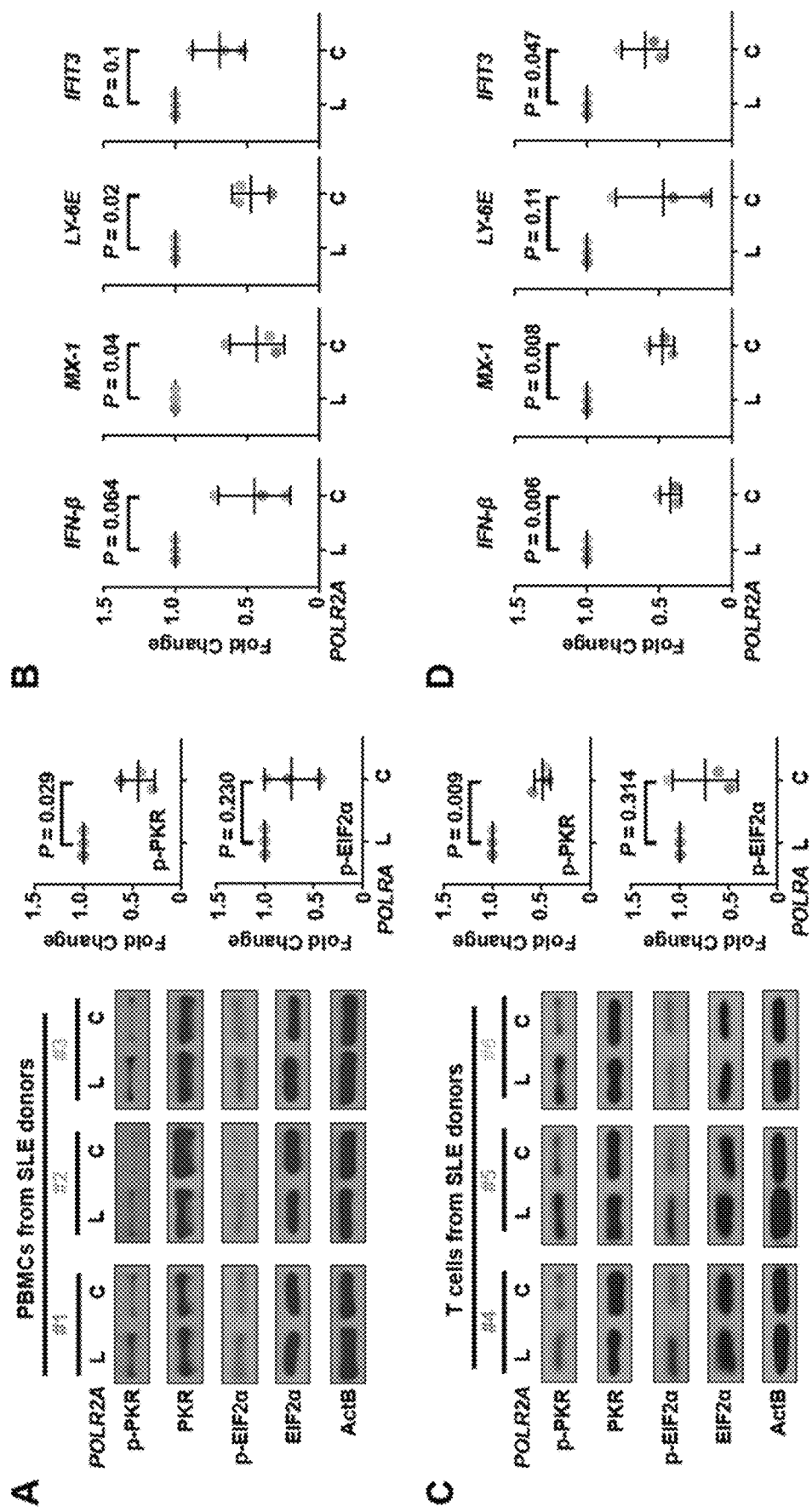
FIG. 6 illustrates phosphorylation level of PKR and downregulated expression of cytokine IFN-beta and diagnostic genes MX-1, LY-6E and IFIT3 for SLE in PBMCs and immune T cells of SLE patients detected after the overexpression of circPOLR2A.

As shown in FIG. 6, after the overexpression of circPOLR2A, the PKR phosphorylation level of mononuclear cells of SLE patients was significantly decreased as compared with a case in which only linear POLR2A was overexpressed. The expression of cytokine IFN-beta and the expression of the diagnostic genes MX-1, LY-6E and IFIT3 for SLE were downregulated. This fully showed that the circPOLR2A could serve as a target, and overexpression of circPOLR2A and the genes of 26 circRNAs of the same type having a special double-stranded structure and expression products thereof could be used to treat SLE.

The foregoing is merely preferred examples of the present disclosure, and is not intended to limit the present disclosure in any form and in essence. It should be noted that several improvements and additions can be made by those of ordinary skill in the art without departing from the method of the present disclosure, and these improvements and additions should also be construed as falling within the protection scope of the present disclosure. Equivalent variations of alterations, modifications and changes made to the technical contents disclosed above by those skilled in the art without departing from the spirit and scope of the present disclosure shall be equivalent examples of the present disclosure, and any alterations, modifications and changes of equivalent variations made to the above examples in accordance with the technical essence of the present disclosure shall falling within the protection scope of the present disclosure.

Example 7

Detection of Expression of Cytokines IFN-Beta, TNFα and IL6 after Transfection of Human HeLa Cells with circPOLR2A Purified In Vitro The cirRNA was successfully prepared through an RNA in vitro transcription experiment and in vitro T4 RNA Ligase circularization, and purified in vitro by using PAGE purification method to obtain high-purity circPOLR2A. The circPOLR2A prepared and purified in vitro was transferred into human HeLa cells by using a liposome transfection method. After transfection for 1 hour or 6 hours, cells were collected for performing Q-PCR to detect the expression of cytokines IFN-beta, TNFα and IL6.

Figure 7:
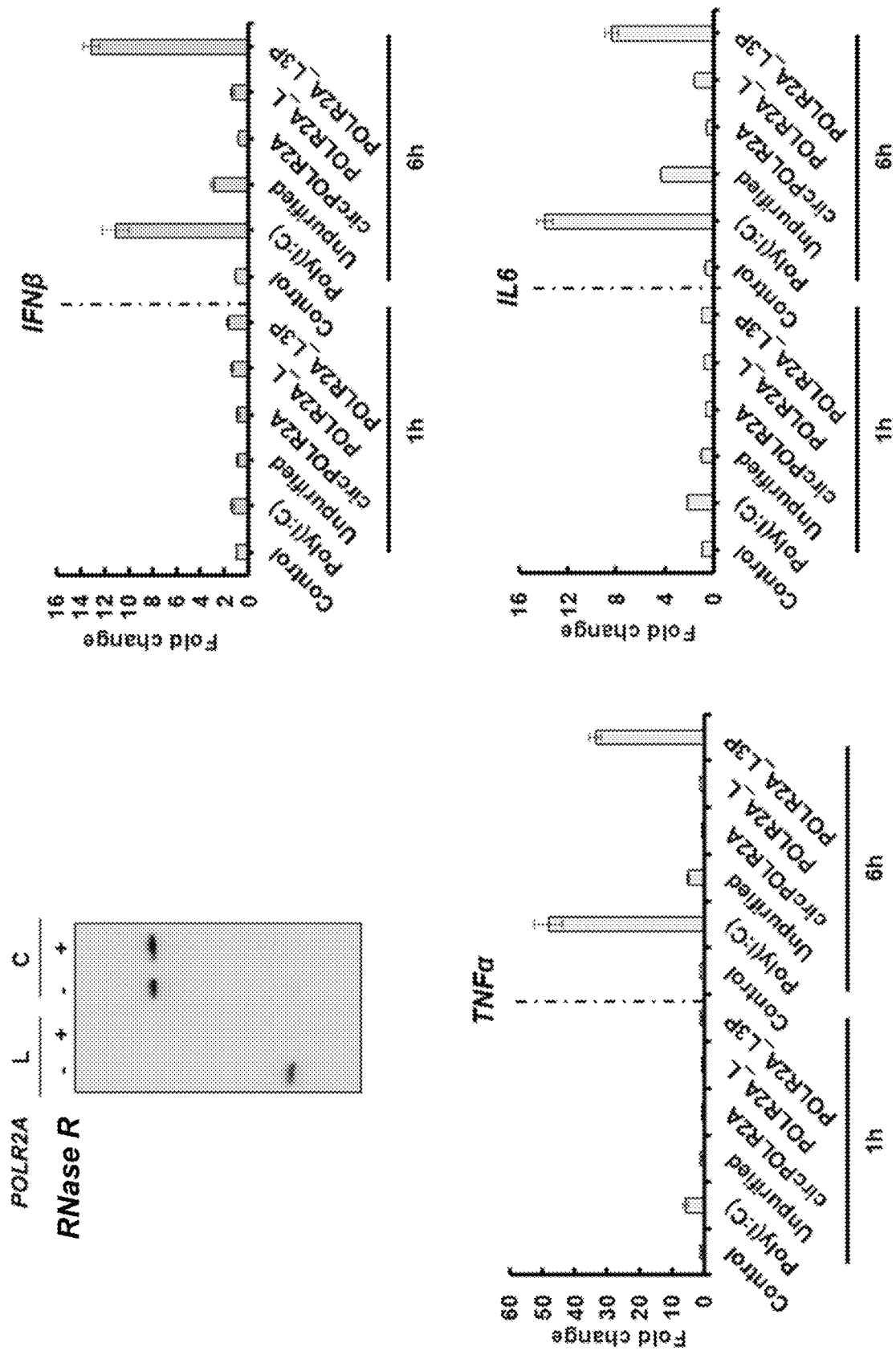
FIG. 7 illustrates expression of cytokines IFN-beta, TNFα and IL6 after introducing circPOLR2A into human HeLa cells.

As shown in FIG. 7, after the circPOLR2A prepared and purified in vitro was transfected into human HeLa cells by using the liposome transfection method, the circPOLR2A prepared and purified in vitro did not cause an increased expression of cytokines IFN-beta, TNFα and IL6 as compared with transfection with double-stranded RNA substrate Poly(I:C), unpurified RNA and linear POLR2A. This fully showed that the circPOLR2A prepared and purified in vitro would not induce immune response. The above experimental results showed that the circPOLR2A prepared and purified in vitro could serve as a target and would not induce unnecessary immune response in the organism.

Example 8

Detection of Regulating Effect of circPOLR2A Purified In Vitro on the Level of PKR Phosphorylation Activation after In Vitro Purification of circPOLR2A and PKR Protein The circRNA was successfully prepared through an RNA in vitro transcription experiment and in vitro T4 RNA Ligase circularization, and purified in vitro by using a PAGE purification method to obtain high-purity circPOLR2A. The PKR protein was successfully prepared by using in vitro purification method with a His tag. The circPOLR2A prepared and purified in vitro was incubated with an experimental system of PKR phosphorylation activation in vitro through a PKR phosphorylation activation experiment in vitro. After reaction at 37° C. for 30 minutes, cells were collected and subjected to isotope $^{32}P$ autoradiography to detect the level of PKR phosphorylation activation.

Figure 8:
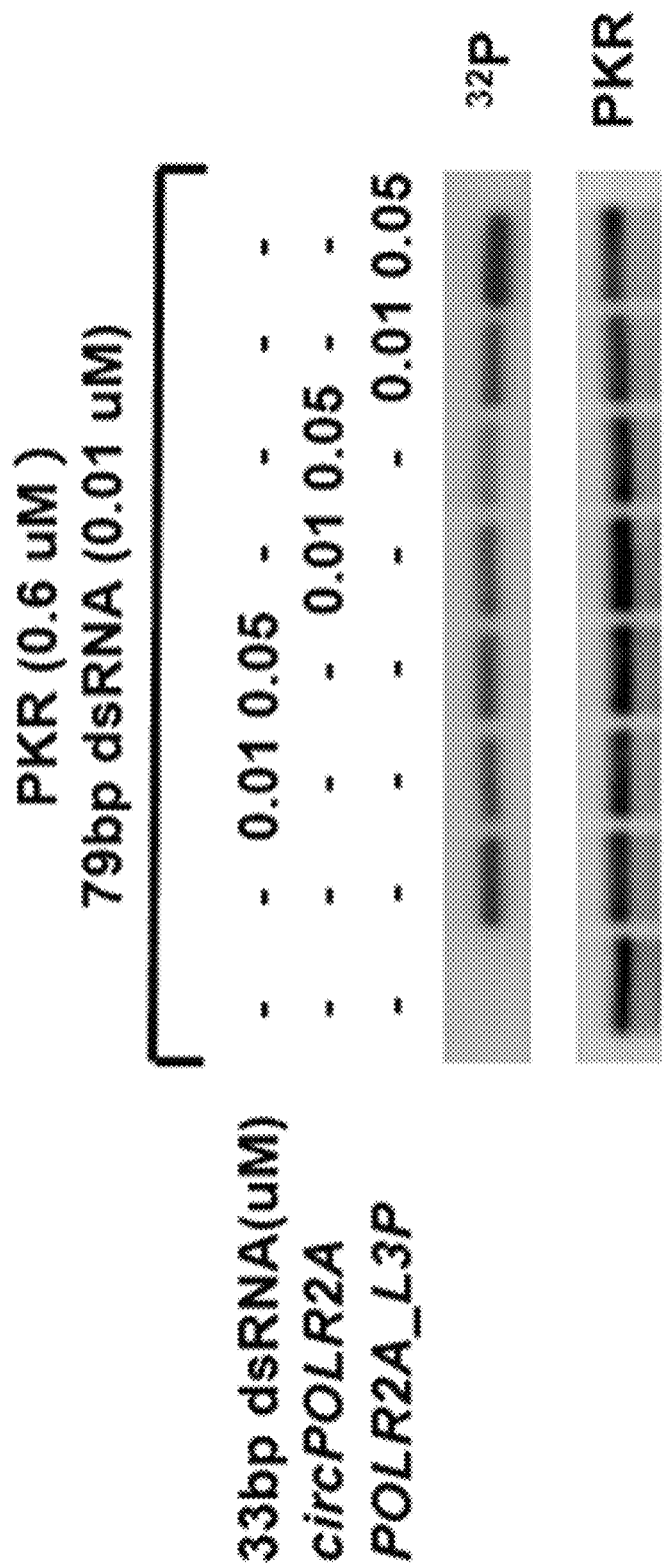
FIG. 8 illustrates a change in the level of PKR phosphorylation activation in vitro after incubation of circPOLR2A with an in vitro experimental system of PKR phosphorylation activation.

As shown in FIG. 8, after the circPOLR2A prepared and purified in vitro was incubated with the experimental system of PKR phosphorylation activation in vitro, the circPOLR2A could cause the level of PKR phosphorylation activation in vitro to decrease significantly as compared with linear POLR2A prepared and purified in vitro. This fully showed that the circPOLR2A could serve as a target, and the circPOLR2A prepared and purified in vitro, the genes of 26 circRNAs of the same type having a special double-stranded structure and expression products thereof could be used to treat SLE.

The foregoing is merely preferred examples of the present disclosure, and is not intended to limit the present disclosure in any form and in essence. It should be noted that several improvements and additions can be made by those of ordinary skill in the art without departing from the method of the present disclosure, and these improvements and additions should also be construed as falling within the protection scope of the present disclosure. Equivalent variations of alterations, modifications and changes made to the technical contents disclosed above by those skilled in the art without departing from the spirit and scope of the present disclosure shall be equivalent examples of the present disclosure, and any alterations, modifications and changes of equivalent variations made to the above examples in accordance with the technical essence of the present disclosure shall falling within the protection scope of the present disclosure.

The invention claimed is:

1. A method of treating systemic lupus erythematosus, comprising administering an effective dose of a circular RNA with an incomplete double-stranded structure of 16 bp-33 bp in length and/or an expression vector overexpressing the circular RNA with an incomplete double-stranded structure of 16 bp-33 bp in length to a subject, wherein the circular RNA with an incomplete double-stranded structure of 16 bp-33 bp in length is circPOLR2A.

2. The method according to claim 1, characterized in that the administering has at least one of the following effects: (1) reducing PKR phosphorylation level in mononuclear cells of a patient with systemic lupus erythematosus; (2) down-regulating the expression of cytokine IFN-beta and diagnostic genes of systemic lupus erythematosus MX-1, LY-6E, IFIT3 in mononuclear cells and immune cell T cells of a patient with systemic lupus erythematosus.

3. The method according to claim 1, characterized in that the circular RNA with an incomplete double-stranded structure of 16 bp-33 bp in length and/or the expression vector overexpressing the circular RNA with an incomplete double-stranded structure of 16 bp-33 bp in length is the only active ingredient or one of the active ingredients for treating systemic lupus erythematosus.

4. The method according to claim 1, characterized in that the method further comprises administering at least one additional medicament for treating systemic lupus erythematosus.

5. A method of treating systemic lupus erythematosus, comprising administering an effective dose of a circular RNA with an incomplete double-stranded structure of 16 bp-33 bp in length and/or an expression vector overexpressing the circular RNA with an incomplete double-stranded structure of 16 bp-33 bp in length to a subject, wherein the circular RNA with an incomplete double-stranded structure of 16 bp-33 bp in length is circCAMSAP1.

6. The method according to claim 5, characterized in that the administering has at least one of the following effects: (1) reducing a PKR phosphorylation level in mononuclear cells of a patient with systemic lupus erythematosus; (2) down-regulating the expression of cytokine IFN-beta and diagnostic genes of systemic lupus erythematosus MX-1, LY-6E, IFIT3 in mononuclear cells and immune cell T cells of a patient with systemic lupus erythematosus.

7. The method according to claim 5, characterized in that the circular RNA with an incomplete double-stranded structure of 16 bp-33 bp in length and/or the expression vector overexpressing the circular RNA with an incomplete double-stranded structure of 16 bp-33 bp in length is the only active ingredient or one of the active ingredients for treating systemic lupus erythematosus.

8. The method according to claim 5, characterized in that the method further comprises administering at least one additional medicament for treating systemic lupus erythematosus.

\* \* \* \* \*

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
aatcggcctg tcatgggtat                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
aaagtctgca ttgtacggag t                                            21

<210> SEQ ID NO 3
<211> LENGTH: 11191
<212> TYPE: DNA
<213> ORGANISM: Artificial Sequence
<220> FEATURE:
<223> OTHER INFORMATION: Synthetic Construct

<400> SEQUENCE: 3
tggaagggct aattcactcc caaagaagac aagatatcct tgatctgtgg atctaccaca    60
```

```
cacaaggcta cttccctgat tagcagaact acacaccagg gccagggtc agatatccac    120 tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag gactttccg     360 ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600 agacccttt agtcagtgtg gaaaatctct agcagtggcg cccgaacagg gacttgaaag     660
cgaaagggaa accagaggag ctctctcgac gcaggactcg gcttgctgaa gcgcgcacgg    720
caagaggcga gggcggcga ctggtgagta cgccaaaaat tttgactagc ggaggctaga     780
aggagagaga tgggtgcgag agcgtcagta ttaagcgggg gagaattaga tcgcgatggg    840
aaaaaattcg gttaaggcca ggggaaaga aaaaatataa attaaaacat atagtatggg     900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtgaa ttggtttaac ataacaaatt ggctgtggta    1800
tataaaatta ttcataatga tagtaggagg cttggtaggt ttaagaatag ttttgctgt    1860 actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccgaa ttcacaaatg   2040
gcagtattca tccacaattt taaaagaaaa ggggggattg ggggtacag tgcagggaa     2100 agaatagtag acataatagc aacagacata caaactaaag aattacaaaa acaaattaca   2160
aaaattcaaa attttcgggt ttattacagg gacagcagag atccagtttg gactagtcgt   2220
gaggctccgg tgcccgtcag tgggcagagc gcacatcgcc cacagtcccc gagaagttgg   2280 ggggagggt cggcaattga accggtgcct agagaaggtg gcgcgggta aactgggaaa     2340 gtgatgtcgt gtactggctc cgcctttttc ccgagggtgg gggagaaccg tatataagtg   2400
```

-continued

```
cagtagtcgc cgtgaacgtt cttttcgca acgggtttgc cgccagaaca caggtaagtg    2460
ccgtgtgtgg ttcccgcggg cctggcctct ttacgggtta tggcccttgc gtgccttgaa    2520
ttacttccac gccctggct gcagtacgtg attcttgatc ccgagcttcg ggttggaagt    2580
gggtgggaga gttcgaggcc ttgcgcttaa ggagccccctt cgcctcgtgc ttgagttgag    2640
gcctggcctg ggcgctgggg ccgccgcgtg cgaatctggt ggcaccttcg cgcctgtctc    2700
gctgctttcg ataagtctct agccatttaa aattttgat gacctgctgc gacgttttt    2760 ttctggcaag atagtcttgt aaatgcgggc caagatctgc acactggtat ttcggttttt    2820
ggggccgcgg gcggcgacgg ggccgtgcg tcccagcgca catgttcggc gaggcggggc    2880
ctgcgagcgc ggccaccgag aatcggacgg gggtagtctc aagctggccg gcctgctctg    2940
gtgcctggcc tcgcgccgcc gtgtatcgcc ccgccctggg cggcaaggct ggcccggtcg    3000
gcaccagttg cgtgagcgga aagatggccg cttcccggcc ctgctgcagg gagctcaaaa    3060
tggaggacgc ggcgctcggg agagcggcg ggtgagtcac ccacacaaag gaaaagggcc    3120
tttccgtcct cagccgtcgc ttcatgtgac tccacggagt accgggcgcc gtccaggcac    3180
ctcgattagt tctcgagctt ttggagtacg tcgtctttag gttgggggga ggggttttat    3240
gcgatggagt ttccccacac tgagtgggtg gagactgaag ttaggccagc ttggcacttg    3300
atgtaattct ccttggaatt tgccctttt gagtttggat cttggttcat tctcaagcct    3360
cagacagtgg ttcaaagttt ttttcttcca tttcaggtgt cgtgaagcgg ccgcaccggt    3420
ctgcagctag ctcgagtcta gaatggtgag caagggcgag gagctgttca ccggggtggt    3480
gcccatcctg gtcgagctgg acggcgacgt aaacggccac aagttcagcg tgtccggcga    3540
gggcgagggc gatgccacct acggcaagct gaccctgaag ttcatctgca ccaccggcaa    3600
gctgcccgtg ccctggccca cctcgtgac cacctgacc tacggcgtgc agtgcttcag    3660
ccgctacccc gaccacatga agcagcacga cttcttcaag tccgccatgc ccgaaggcta    3720
cgtccaggca cgtagcaggc cagggcctct ctcagccacc tgagcagaaa gctttccaag    3780
atagggcagg ctgggttagg ccatctgagt ctgtctcgtt cattgggatc cagacttgac    3840
tgtcttgtta aaggctgttg ctgcccaggt gtgcagggag ctgttggtct ctggcattca    3900 gggtggggt ggtataaacc cggggcagct tgcatatggc agggaagagg gatccgtgga    3960
ggaacagtgc agaaggcttt atgttcagaa tctctcttgc ttttcttcta gactgagttc    4020
cttgagattg gtgaatgctg tgtattattc atccctgata acctggtgtt tggcccaggg    4080
ccttgtccag aggagtgttt gataagtgtt tcaagtgaat tagcaccacg atgtcatctc    4140
ttttcagttt acaaaggacg gacacccct gacccggtct cagaaagcct gaaagcagaa    4200
ttagtcatta aagggtggt tggcttggtc ggcatagact ttgagcagaa agaggttgaa    4260
aatgttgagc ctgatttctc ttaggccct ctgcagtgtc tgttgtggag gccagatacg    4320
taactgcttc cgctttttt ggtctcattc aaggtgagca aatcccttc atgtttctca    4380 ccagacaatg cagctgatga ggttccagct ttgcaaatgt agtcatccat gaggactgtc    4440
ttcctgagat ttcatcaggc tcgagggact tgcaaaggac tttaggtcca ttgtccttt    4500 attcttgat acctctttca ctgagacctt ttccttacct cacctctcta ggtggaacgg    4560
cacatgtgtg atggggacat tgttatcttc aaccggcagc caactctgca caaaatgtcc    4620 atgatgggc atcgggtccg cattctccca tggtctacct ttcgcttgaa tcttaggtca    4680
gtccctggct gagggaagca ggctggaatt ggtgggaggc gggcaggctg ggtggctcct    4740
caaggtttcg ctgcagacat cttcccaacc ctgactttc tctttaactg tagtgtgaca    4800
```

```
actccgtaca atgcagactt tgacggggat gagatgaact tgcacctgcc acagtctctg    4860
gagacgcgag cagagatcca ggagctggcc atggttcctc gcatgattgt cacccccag    4920 agcaatcggc ctgtcatggg tattgtgcag acacactca cagcagtgcg caaattcacc    4980
aagagagacg tcttcctgga gcgggtgtgt ggtccaaatg gaaacctggc ttaagtgggc    5040
agtggggctc tggggtgcaa ggtggaggct agagaggaag agctgtgttt ttttcctga    5100 cttacccagc agtggtctgt gagattgtct tttctggtgg gcgaacaaaa aggggttag    5160 gaaaactcag gccaaaaaag tgtaaggcgt taattcccca tttaattcct taaaatttca    5220
tgtaatacca ggtattgcct gtaaaggaaa gataaaggga aaaataagta agaccttgtt    5280 aaaatttat ttttctattt taaccttcac ttatttccta attattaaaa gaaatttatg    5340
cttattgtta agaacaaaaa aatttcagta ttacaatgaa tttttaatta aaagtttttg    5400
gcctgatgaa atctcaggaa gacagtcctc atggatgact acatttgcaa agctggaacc    5460
tcatcagctg cattgtctgg tgagaaacat gaagggggatt tgctcacctt gaatgagacc    5520
aaaaaaagcg gaagcagtta cgtatctggc ctccacaaca gacactgcag aggggcctaa    5580
gagaaatcag gctcaacatt ttcaacctct ttctgctcaa agtctatgcc gaccaagcca    5640
accacccttc taatgactaa ttctgctttc aggctttctg agaccgggtc aggggggtgtc    5700 cttaaaggtt ggaaaaaact tttcctgtca tctttgcctc caaaatctgg cttttctccct    5760 tgggcaggga aacctcccca acatttctct atcatccctg agatgtgggg cctgcactct    5820
gacttctgtc tgccttactc tttgtcttac aggagcgcac catcttcttc aaggacgacg    5880
gcaactacaa gacccgcgcc gaggtgaagt tcgagggcga caccctggtg aaccgcatcg    5940
agctgaaggg catcgacttc aaggaggacg gcaacatcct ggggcacaag ctggagtaca    6000
actacaacag ccacaacgtc tatatcatgg ccgacaagca gaagaacggc atcaaggtga    6060
acttcaagat ccgccacaac atcgaggacg gcagcgtgca gctcgccgac cactaccagc    6120
agaacacccc catcggcgac ggccccgtgc tgctgcccga caaccactac ctgagcaccc    6180
agtccgccct gagcaaagac cccaacgaga gcgcgatca catggtcctg ctggagttcg    6240
tgaccgccgc cgggatcact ctcggcatgg acgagctgta caagtaagga tccctccccc    6300
ccccctaacg ttactggccg aagccgcttg gaataaggcc ggtgtgcgtt tgtctatatg    6360
ttattttcca ccatattgcc gtcttttggc aatgtgaggg cccggaaacc tggccctgtc    6420
ttcttgacga gcattcctag gggtctttcc cctctcgcca aaggaatgca aggtctgttg    6480
aatgtcgtga aggaagcagt tcctctggaa gcttcttgaa gacaaacaac gtctgtagcg    6540 acccctttgca ggcagcggaa ccccccacct ggcgacaggt gcctctgcgg ccaaaagcca    6600
cgtgtataag atacacctgc aaaggcggca caacccccagt gccacgttgt gagttggata    6660
gttgtggaaa gagtcaaatg gctctcctca agcgtattca acaaggggct gaaggatgcc    6720
cagaaggtac cccattgtat gggatctgat ctggggcctc ggtgcacatg ctttacatgt    6780
gtttagtcga ggttaaaaaa acgtctaggc ccccgaacc acggggacgt ggttttcctt    6840
tgaaaaacac gatgataata tggccacaca tatgcccag tccaagcacg gcctgaccaa    6900
ggagatgacc atgaagtacc gcatggaggg ctgcgtggac ggccacaagt tcgtgatcac    6960
cggcgagggc atcggctacc ccttcaaggg caagcaggcc atcaacctgt gcgtggtgga    7020
gggcggcccc ttgccccttcg ccgaggacat cttgtccgcc gccttcatgt acggcaaccg    7080
cgtgttcacc gagtaccccc aggacatcgt cgactacttc aagaactcct gccccgccgg    7140
```

```
ctacacctgg gaccgctcct tcctgttcga ggacggcgcc gtgtgcatct gcaacgccga    7200
catcaccgtg agcgtggagg agaactgcat gtaccacgag tccaagttct acggcgtgaa    7260
cttccccgcc gacggccccg tgatgaagaa gatgaccgac aactgggagc cctcctgcga    7320
gaagatcatc cccgtgccca agcagggcat cttgaagggc gacgtgagca tgtacctgct    7380
gctgaaggac ggtggccgct gcgctgcca gttcgacacc gtgtacaagg ccaagtccgt    7440
gccccgcaag atgcccgact ggcacttcat ccagcacaag ctgacccgcg aggaccgcag    7500
cgacgccaag aaccagaagt ggcacctgac cgagcacgcc atcgcctccg gctccgcctt    7560
gccctgaatc gatagatcct aatcaacctc tggattacaa aatttgtgaa agattgactg    7620
gtattcttaa ctatgttgct ccttttacgc tatgtggata cgctgcttta atgcctttgt    7680
atcatgctat tgcttcccgt atggctttca ttttctcctc cttgtataaa tcctggttgc    7740
tgtctcttta tgaggagttg tggcccgttg tcaggcaacg tggcgtggtg tgcactgtgt    7800
ttgctgacgc aaccccact ggttgggca ttgccaccac ctgtcagctc ctttccggga    7860
ctttcgcttt cccctccct attgccacgg cggaactcat cgccgcctgc cttgcccgct    7920
gctggacagg ggctcggctg ttgggcactg acaattccgt ggtgttgtcg gggaaatcat    7980 cgtccttttcc ttggctgctc gcctgtgttg ccacctggat tctgcgcggg acgtccttct    8040
gctacgtccc ttcggccctc aatccagcgg accttccttc ccgcggcctg ctgccggctc    8100
tgcggcctct tccgcgtctt cgccttcgcc ctcagacgag tcggatctcc ctttgggccg    8160
cctccccgcc tgagatcctt taagaccaat gacttacaag gcagctgtag atcttagcca    8220 cttttttaaaa gaaaaggggg gactggaagg gctaattcac tcccaacgaa gacaagatct    8280 gcttttttgct tgtactgggt ctctctggtt agaccagatc tgagcctggg agctctctgg    8340
ctaactaggg aacccactgc ttaagcctca ataaagcttg ccttgagtgc ttcaagtagt    8400
gtgtgcccgt ctgttgtgtg actctggtaa ctagagatcc ctcagaccct tttagtcagt    8460
gtggaaaatc tctagcagta gtagttcatg tcatcttatt attcagtatt tataacttgc    8520
aaagaaatga atatcagaga gtgagaggcc cgggttaatt aaggaaaggg ctagatcatt    8580
cttgaagacg aaagggcctc gtgatacgcc tatttttata ggttaatgtc atgataataa    8640
tggtttctta gacgtcaggt ggcacttttc ggggaaatgt gcgcggaacc cctatttgtt    8700
tatttttcta aatacattca aatatgtatc cgctcatgag acaataaccc tgataaatgc    8760
ttcaataata ttgaaaaagg aagagtatga gtattcaaca tttccgtgtc gcccttattc    8820 cctttttgc ggcattttgc cttcctgttt ttgctcaccc agaaacgctg gtgaaagtaa    8880
aagatgctga agatcagttg ggtgcacgag tgggttacat cgaactggat ctcaacagcg    8940
gtaagatcct tgagagtttt cgccccgaag aacgttttcc aatgatgagc acttttaaag    9000
ttctgctatg tggcgcggta ttatcccgtg ttgacgccgg gcaagagcaa ctcggtcgcc    9060
gcatacacta ttctcagaat gacttggttg agtactcacc agtcacagaa aagcatctta    9120
cggatggcat gacagtaaga gaattatgca gtgctgccat aaccatgagt gataacactg    9180
cggccaactt acttctgaca acgatcggag gaccgaagga gctaaccgct ttttttgcaca    9240 acatggggga tcatgtaact cgccttgatc gttgggaacc ggagctgaat gaagccatac    9300
caaacgacga gcgtgacacc acgatgcctg tagcaatggc aacaacgttg cgcaaactat    9360
taactggcga actacttact ctagcttccc ggcaacaatt aatagactgg atggaggcgg    9420
ataaagttgc aggaccactt ctgcgctcgg cccttccggc tggctggttt attgctgata    9480
aatctggagc cggtgagcgt gggtctcgcg gtatcattgc agcactgggg ccagatggta    9540
```

```
agccctcccg tatcgtagtt atctacacga cggggagtca ggcaactatg gatgaacgaa    9600
atagacagat cgctgagata ggtgcctcac tgattaagca ttggtaactg tcagaccaag    9660
tttactcata tatactttag attgatttaa aacttcattt ttaatttaaa aggatctagg    9720
tgaagatcct ttttgataat ctcatgacca aaatcccttta acgtgagttt tcgttccact   9780
gagcgtcaga ccccgtagaa aagatcaaag gatcttcttg agatcctttt tttctgcgcg    9840
taatctgctg cttgcaaaca aaaaaaccac cgctaccagc ggtggtttgt ttgccggatc    9900
aagagctacc aactcttttt ccgaaggtaa ctggcttcag cagagcgcag ataccaaata    9960
ctgttcttct agtgtagccg tagttaggcc accacttcaa gaactctgta gcaccgccta   10020
catacctcgc tctgctaatc ctgttaccag tggctgctgc cagtggcgat aagtcgtgtc   10080
ttaccgggtt ggactcaaga cgatagttac cggataaggc gcagcggtcg ggctgaacgg   10140
ggggttcgtg cacacagccc agcttggagc gaacgaccta caccgaactg agatacctac   10200
agcgtgagct atgagaaagc gccacgcttc ccgaagggag aaaggcggac aggtatccgg   10260
taagcggcag ggtcggaaca ggagagcgca cgagggagct tccaggggga aacgcctggt   10320
atctttatag tcctgtcggg tttcgccacc tctgacttga gcgtcgattt ttgtgatgct   10380
cgtcaggggg gcggagccta tggaaaaacg ccagcaacgc ggcctttttta cggttcctgg   10440 ccttttgctg gccttttgct cacatgttct ttcctgcgtt atcccctgat tctgtggata   10500
accgtattac cgcctttgag tgagctgata ccgctcgccg cagccgaacg accgagcgca   10560
gcgagtcagt gagcgaggaa gcggaagagc gcccaatacg caaaccgcct ctccccgcgc   10620
gttggccgat tcattaatgc agcaagctca tggctgacta attttttttta tttatgcaga   10680 ggccgaggcc gcctcggcct ctgagctatt ccagaagtag tgaggaggct ttttttggagg   10740 cctaggcttt tgcaaaaagc tccccgtggc acgacaggtt tcccgactgg aaagcgggca   10800
gtgagcgcaa cgcaattaat gtgagttagc tcactcatta ggcacccag gctttacact    10860 ttatgcttcc ggctcgtatg ttgtgtggaa ttgtgagcgg ataacaattt cacacaggaa   10920
acagctatga catgattacg aatttcacaa ataaagcatt tttttcactg cattctagtt   10980
gtggtttgtc caaactcatc aatgtatctt atcatgtctg gatcaactgg ataactcaag   11040
ctaaccaaaa tcatcccaaa cttcccaccc catacctat taccactgcc aattacctgt    11100
ggtttcattt actctaaacc tgtgattcct ctgaattatt ttcattttaa agaaattgta   11160
tttgttaaat atgtactaca aacttagtag t                                  11191
```